(12) United States Patent
Pancholy et al.

(10) Patent No.: US 11,564,697 B2
(45) Date of Patent: Jan. 31, 2023

(54) APPARATUS AND METHOD TO STOP BLEEDING

(71) Applicants: Samir Bipin Pancholy, Clarks Summit, PA (US); Nolan Rajendra Sardesai, Arcadia, CA (US); Milind Padmakar Panse, Riverside, CA (US); Rajendra Gurudas Sardesai, Arcadia, CA (US)

(72) Inventors: Samir Bipin Pancholy, Clarks Summit, PA (US); Nolan Rajendra Sardesai, Arcadia, CA (US); Milind Padmakar Panse, Riverside, CA (US); Rajendra Gurudas Sardesai, Arcadia, CA (US)

(73) Assignee: Vasoinnovations Inc., South Pasadena, CA (US)

( * ) Notice: Subject to any disclaimer, the term of this patent is extended or adjusted under 35 U.S.C. 154(b) by 139 days.

(21) Appl. No.: 17/005,262

(22) Filed: Aug. 27, 2020

(65) Prior Publication Data
US 2020/0390448 A1 Dec. 17, 2020

Related U.S. Application Data

(63) Continuation of application No. 16/130,201, filed on Sep. 13, 2018, now abandoned, which is a
(Continued)

(51) Int. Cl.
*A61B 17/132* (2006.01)
*A61B 17/135* (2006.01)
(Continued)

(52) U.S. Cl.
CPC ........ *A61B 17/1325* (2013.01); *A61B 5/0295* (2013.01); *A61B 17/135* (2013.01);
(Continued)

(58) Field of Classification Search
CPC .............. A61B 17/1325; A61B 17/135; A61B 2017/00889; A61B 2017/00902; A61B 17/3215; A61B 2017/12004; A61B 5/0295
See application file for complete search history.

(56) References Cited

U.S. PATENT DOCUMENTS

| 37,156 A | 12/1862 | Dunton |
| 3,905,361 A | 9/1975 | Hewson et al. |
(Continued)

FOREIGN PATENT DOCUMENTS

| EP | 0 601 756 A1 | 6/1994 |
| EP | 1 382 306 A2 | 1/2004 |
(Continued)

OTHER PUBLICATIONS

U.S. Appl. No. 13/933,025, filed Jul. 1, 2013, Wada et al.
(Continued)

*Primary Examiner* — Jing Rui Ou
(74) *Attorney, Agent, or Firm* — Rajendra Gurudas Sardesai

(57) ABSTRACT

A hemostatic device is provided to stop bleeding at a puncture site on the wrist of a patient, the device comprising a transparent flexible band to be wrapped at the site where the bleeding is to be stopped, a curved frame having an inner peripheral side and possessing a first curved portion in its first half and a second curved portion in its second half, a first balloon provided on the inner peripheral side in the first half of the curved frame and a second balloon provided on the inner peripheral side in the second half of the curved frame. The bleeding from a first artery is stopped by compressing the first artery at the puncture site using infla-
(Continued)

tion of the first balloon and the blood flow in the first artery is increased by compression of a second artery using inflation of the second balloon.

16 Claims, 13 Drawing Sheets

Related U.S. Application Data continuation of application No. 15/588,586, filed on May 5, 2017, now Pat. No. 10,335,161, which is a continuation of application No. 15/150,394, filed on May 9, 2016, now Pat. No. 9,668,744, which is a continuation-in-part of application No. 14/819,383, filed on Aug. 5, 2015, now Pat. No. 9,332,994, which is a continuation-in-part of application No. 13/941,219, filed on Jul. 12, 2013, now Pat. No. 9,308,000.

(60) Provisional application No. 62/288,982, filed on Jan. 29, 2016, provisional application No. 62/142,195, filed on Apr. 2, 2015, provisional application No. 62/103,063, filed on Jan. 13, 2015, provisional application No. 62/096,857, filed on Dec. 25, 2014, provisional application No. 62/089,281, filed on Dec. 9, 2014.

(51) Int. Cl.
| | | |
|---|---|---|
| *A61B 17/12* | (2006.01) | |
| *A61B 5/0295* | (2006.01) | |
| *A61B 17/3215* | (2006.01) | |
| *A61B 17/00* | (2006.01) | |

(52) U.S. Cl.
CPC ............. *A61B 17/3215* (2013.01); *A61B 2017/00889* (2013.01); *A61B 2017/00902* (2013.01); *A61B 2017/12004* (2013.01)

(56) References Cited

U.S. PATENT DOCUMENTS

| | | | |
|---|---|---|---|
| 4,469,099 | A | 9/1984 | Mc Ewen |
| 4,863,429 | A | 9/1989 | Baldwin |
| 4,920,971 | A | 5/1990 | Blessinger |
| 4,981,133 | A | 1/1991 | Rollband |
| 5,152,302 | A | 10/1992 | Fareed |
| 5,295,951 | A | 3/1994 | Fareed |
| 5,307,811 | A | 5/1994 | Sigwart et al. |
| 5,413,582 | A | 5/1995 | Eaton |
| 5,433,724 | A | 7/1995 | Kawasaki et al. |
| 5,464,420 | A | 11/1995 | Hori et al. |
| 5,486,194 | A | 1/1996 | Kawasaki et al. |
| 5,496,262 | A | 3/1996 | Johnson et al. |
| 5,514,155 | A | 5/1996 | Daneshvar |
| 5,569,297 | A | 10/1996 | Makower et al. |
| 5,643,315 | A | 7/1997 | Daneshvar |
| 5,660,182 | A | 8/1997 | Kuroshaki et al. |
| 5,690,610 | A | 11/1997 | Ito et al. |
| 5,779,657 | A | 7/1998 | Daneshvar |
| 5,792,173 | A | 8/1998 | Breen et al. |
| 5,840,037 | A | 11/1998 | Tochikubo et al. |
| 6,007,562 | A | 12/1999 | Harren et al. |
| 6,336,901 | B1 | 1/2002 | Itonaga et al. |
| 6,361,496 | B1 | 3/2002 | Zikorus et al. |
| 6,527,727 | B2 | 3/2003 | Itonaga et al. |
| 6,694,821 | B2 | 2/2004 | Yamakoshi et al. |
| 6,827,727 | B2 | 12/2004 | Stalemark et al. |
| 7,498,477 | B2 | 3/2009 | Wada et al. |
| 7,927,295 | B2 | 4/2011 | Bates et al. |
| 8,034,009 | B2 | 10/2011 | Bates et al. |
| 8,152,776 | B2 | 4/2012 | McCluskey |
| 8,481,803 | B2 | 7/2013 | Wada et al. |
| 8,481,805 | B2 | 7/2013 | Wada et al. |
| 8,524,974 | B2 | 9/2013 | Wada et al. |
| 8,759,603 | B2 | 6/2014 | Wada et al. |
| 9,895,155 | B2 | 2/2018 | Wada et al. |
| 2002/0115603 | A1 | 8/2002 | Whitehouse |
| 2002/0147404 | A1 | 10/2002 | Kato |
| 2002/0170359 | A1 | 11/2002 | Yamakoshi et al. |
| 2003/0199922 | A1 | 10/2003 | Buckman |
| 2004/0049214 | A1 | 3/2004 | Akerfeldt |
| 2004/0098035 | A1 | 5/2004 | Wada et al. |
| 2004/0122469 | A1 | 6/2004 | Akerfeldt |
| 2004/0193059 | A1 | 9/2004 | Inoue et al. |
| 2005/0153090 | A1 | 7/2005 | Marchitto |
| 2006/0149153 | A1 | 7/2006 | Shirasaki et al. |
| 2009/0138039 | A1 | 5/2009 | Wada et al. |
| 2009/0234261 | A1 | 9/2009 | Singh |
| 2009/0281565 | A1 | 11/2009 | McNeese |
| 2010/0179586 | A1 | 7/2010 | Ward et al. |
| 2012/0071804 | A1 | 3/2012 | Philip et al. |
| 2012/0296369 | A1 | 11/2012 | Atthoff et al. |
| 2013/0023734 | A1* | 1/2013 | Okamura .......... A61M 25/0097 600/227 |
| 2013/0116725 | A1 | 5/2013 | Wada et al. |
| 2013/0178894 | A1 | 7/2013 | Wada et al. |
| 2013/0237866 | A1 | 9/2013 | Cohen |
| 2013/0245674 | A1 | 9/2013 | Wada et al. |
| 2013/0245675 | A1 | 9/2013 | Wada et al. |
| 2013/0282048 | A1 | 10/2013 | Wada et al. |
| 2013/0289613 | A1 | 10/2013 | Wada et al. |
| 2014/0142615 | A1 | 5/2014 | Corrigan, Jr. |
| 2015/0018869 | A1 | 1/2015 | Benz |
| 2015/0201948 | A1 | 7/2015 | Kornowski et al. |
| 2016/0174952 | A1 | 7/2016 | Shah |
| 2016/0213373 | A1 | 7/2016 | Drasler et al. |
| 2016/0338709 | A1 | 11/2016 | Wada et al. |
| 2018/0000491 | A1 | 1/2018 | Wada et al. |
| 2018/0000492 | A1 | 1/2018 | Wada et al. |
| 2018/0000493 | A1 | 1/2018 | Wada et al. |
| 2018/0000494 | A1 | 1/2018 | Wada et al. |
| 2018/0014833 | A1 | 1/2018 | Wada et al. |

FOREIGN PATENT DOCUMENTS

| | | |
|---|---|---|
| EP | 2 070 483 A2 | 6/2009 |
| EP | 2 245 998 A1 | 11/2010 |
| GB | 2486194 A | 6/2012 |
| JP | 56-33526 Y2 | 8/1981 |
| JP | 5-305093 A | 11/1993 |
| JP | 7-79983 A | 3/1995 |
| JP | 8-71077 A | 3/1996 |
| JP | 8-140990 A | 6/1996 |
| JP | 3031486 U | 9/1996 |
| JP | 10-57386 A | 3/1998 |
| JP | 2000-515773 A | 11/2000 |
| SG | 178650 A1 | 3/2012 |
| WO | WO 97/02783 A1 | 1/1997 |
| WO | WO-97/17900 A1 | 5/1997 |
| WO | WO-2012/126154 A1 | 9/2012 |

OTHER PUBLICATIONS

U.S. Appl. No. 13/889,101, filed May 7, 2013, Wada et al.
U.S. Appl. No. 13/889,112, filed May 7, 2013, Wada et al.
U.S. Appl. No. 15/229,455, filed Aug. 5, 2016, Wada et al.
U.S. Appl. No. 15/705,483, filed Sep. 15, 2017, Wada et al.
U.S. Appl. No. 15/705,570, filed Sep. 15, 2017, Wada et al.
U.S. Appl. No. 15/705,994, filed Sep. 15, 2017, Wada et al.
U.S. Appl. No. 15/706,301, filed Sep. 15, 2017, Wada et al.
U.S. Appl. No. 15/706,397, filed Sep. 15, 2017, Wada et al.
Samir Pancholy, et al, "Prevention of Radial Artery Occlusion—Patent Hemostasis Evaluation Trial (Prophet study)" Catheterization and Cardiovascular Interv 72:335-340 (2008).
Samir B. Pancholy, "Transradial Access in an Occluded Radial Artery: New Technique" Journal Invasive Cardiology, vol. 19, Issue 12, Dec. 2007.
Samir B. Pancholy, "Transradial Approach" Angioplasty.Org Interview Series, 3 pages, Aug. 2008.

(56) References Cited

OTHER PUBLICATIONS

Samir B. Pancholy, "Impact of Two Different Hemostatic Devices on Radial Artery Outcomes after Transradial Catheterization" J Invasive Cardiology,vol. 21,Issue 3, Mar. 2009.
Ivo Bernat, et al, "Efficacy and Safety of Transient Ulnar Artery Compression to Recanalize Actute Radial Artery Occlusion . . . " Am J Cardiol,107:1698-1701 (2011).
Samir B. Pancholy, "Strategies to Prevent Radial Artery Occlusion After Transradial PCI" Curr Cardiol Rep, 16:505, Jun. 2014.
International Search Report in International application No. PCT/US 16/41801.
Written Opinion of The International Searching Authority in International application No. PCT/US 16/41801.
Search History in International application No. PCT/US 1641801.
Patel, T. et al, "Balloon-assisted tracking: A must-know technique . . . " Cath. Cardio. Interv., Wileyonlinelibrary.com; DOI:10.1002/ccd.24959, Apr. 2013.
Kwan, T. et al, "Transulnar catheterization in patients with ipsilateral radial artery occlusion" Cath Cardio Interv, Wileyonlinelibrary.com, DOI 10.1002/ccd.24662 Sep. 2012.
Patel, T. et al, "Balloon-assisted tracking of a guide catheter . . . : A technical report" Cath. Cardio. Interv., Wileyonlinelibrary.com; DOI 10.1002/ccd.24504, May 2012.
Kwan, T. et al. "Feasibility and safety of 7F sheathless guiding catheter during transradial coronary intervention", Wileyonlinelibrary.com; DOI 10.1002/ccd.24310, Aug. 2012.
Pancholy, S et al, "Comparison of a priori versus provisional heparin therapy on radial artery occlusion . . . (Pharaoh Study)", Am J Cardiol, vol. 110(2), p. 173-176 Jul. 2012.
Pancholy, S et al, "Radial artery access technique evaluation trial: randomized comparison . . . ", Catheter Cardiovasc Interv., vol. 80(2), p. 288-91, Aug. 2012.
Pancholy, S et al, "Effect of duration of hemostatic compression on radial artery occlusion after transradial access", Catheter Cardio Interv, vol. 79(1), p. 78-81, Jan. 2012.
Caputo, R, et al, "Transradial arterial access for coronary and peripheral procedures . . . " Catheter Cardiovasc Interv., vol. 78(6), p. 823-39, Nov. 2011.
Bertrand, O et al, "Transradial approach for coronary angiography and interventions . . . ", JACC Cardiovasc Interv., vol. 3(10), p. 1022-31 Oct. 2010.
Pancholy, S et al, "Comparison of door-to-balloon times for primary PCI using transradial versus transfemoral approach" Catheter Cardio Interv. vol. 75(7), p. 991-5 Jun. 2010.
International Search Report in International application No. PCT/US 16/45207.
Written Opinion of The International Searching Authority in International application No. PCT/US 16/45207.
European Search Report Application No. EP 16181506.
International Preliminary Report on Patentability (Chapter 1 of PCT) International Application No. PCT/US2016/041801.
International Preliminary Report on Patentability (Chapter 1 of PCT) International Application No. PCT/US2016/045207.
Extended European Search Report Application No. EP 16833489.
Letter regarding Commonly Assigned Copending and Allowed Applications.
Patel, T. et al, "Contralateral transradial approach for carotid artery stenting: a feasibility study" J. Catheter Cardiovasc Interv. vol. 75(2), p. 268-75. Feb. 2010.
Pancholy, S. "Comparison of the effect of intra-arterial versus intravenous heparin on radial artery occlusion . . . " Am J Cardiol. vol. 104(8) p. 1083-5 Oct. 2009.

Pancholy, S. "Prevention of Radial Artery Occlusion:Prophylactic Hyperperfusion Evaluation Trial ( Prophet-II)" ClinicalTrial.Gov, Protocol Registration System, Mar. 2012.
Pancholy, S. et al, "Subcutaneous administration of nitroglycerin to facilitate radial artery cannulation" Catheter Cardiovasc Interv. vol. 68(3) p. 389-9, Sep. 2006.
Mamas, M, "Dissection, Occlusion, and Spasm; Myths Involving Sheathless Guide Catheters" Catheterization and Cardiovascular Interventions 76:777-778, Feb. 2010.
Pancholy, S "Hemostasis and Radial Artery Patency", Presentation, http://www.slideshare.net/theradialist/pancholy-sb-201111, Jan. 2012.
Shroff, A et al "Comparing radial with femoral artery access in patients with ST-segment elevation myocardial infarction . . . " Expert Rev Cardio Ther. 11(5):525-7, May 2013.
Patel, T et al "Coronary cannulation through mirror-image right aortic arch during right transradial approach . . . " J Invasive Cardiol. 24(5):234-5, May 2012.
Kwan, T. et al "Balloon-assisted sheathless transradial intervention (BASTI) using 5 Fr guiding catheters" J Invasive Cardiol. 24(5):231-3, May 2012.
Dharma, S. et al "Nitroglycerin plus diltiazem versus nitroglycerin alone for spasm prophylaxis with transradial approach" J Invasive Cardiol. 24(3):122-5, Mar. 2012.
Examiner's Search in priority U.S. Appl. No. 13/941,219, filed Jul. 12, 2013—Other References Patent.
Examiner's Search in priority U.S. Appl. No. 13/941,219, filed Jul. 12, 2013—Other References NPL.
Examiner's Search in priority U.S. Appl. No. 13/941,219, filed Jul. 12, 2013—Other References Inventor.
Pancholy, S. et al Prevention of radial artery occulusion . . . , The Prophet-II Randomized trial, JACC: Cardiovascular Interventions, vol. 9 (19), pp. 1992-1999, Oct. 2016.
Maden, O. et al "Relation between end-procedural activated clotting time values . . . after transradial catheterization" Am. J. Cardiol., vol. 118, pp. 1455-1459 (2016).
Hahalis, G. et al "A comparison of low versus standard heparin dose . . . after 5 French coronary angiography" Int. J. Cardiol. vol. 187, pp. 404-410 (2015).
Aykan, A. et al "Comparison of low dose versus standard dose heparin for radial approach in elective coronary angiography" Int. J. Cardiol. vol. 187, pp. 389-392 (2015).
Uhlemann, M. et al. "The leipzig prospective vascular ultrasound registry in radial artery catheterization", JACC: Cardiovascular Interventions, vol. 5, No. 1, pp. 36-43 (2012).
Roghani, R. et al "The effect of low dose versus standard dose of arterial heparin . . . randomized clinical trial", ARYA Atheroscler, vol. 12 (1), pp. 10-17 (2016).
Kiemeneij, F. et al. "The Prophet-II's Prophecy", JACC: Cardiovascular Interventions, vol. 9, No. 19, pp. 2000-2001, Oct. 2016.
Extended European Search Report Application No. EP 18163282.
Pancholy, S., "Radial Artery Hemostasis and Occlusion", Presentation, TCT 2012, Miami, FL.
Pancholy, S., "Radial Shealth Removal and Prevention of Radial Occlusion", Presentation, TCT 2012, Miami, FL.
Pancholy, S et al "A technique to access difficult to find upper extremity veins for right heart catheterization . . . " Catheter Cardiovasc Interv., 78(5):809-12, Nov. 2011.
Patel, T et al, "Reaccessing an occluded radial artery: a "proximal entry" technique" J Interv Cardiol. 24(4):378-81, Aug. 2011.
Patel, T et al, "Management of radial and brachial artery perforations during transradial procedures . . . " J Invasive Cardiol. 21(10):544-7, Oct. 2009.
Patel, T et al, "A simple approach for the reduction of knotted coronary catheter in radial artery during transradial approach" J Invasive Cardiol. 23(5):E126-7, May 2011.

\* cited by examiner

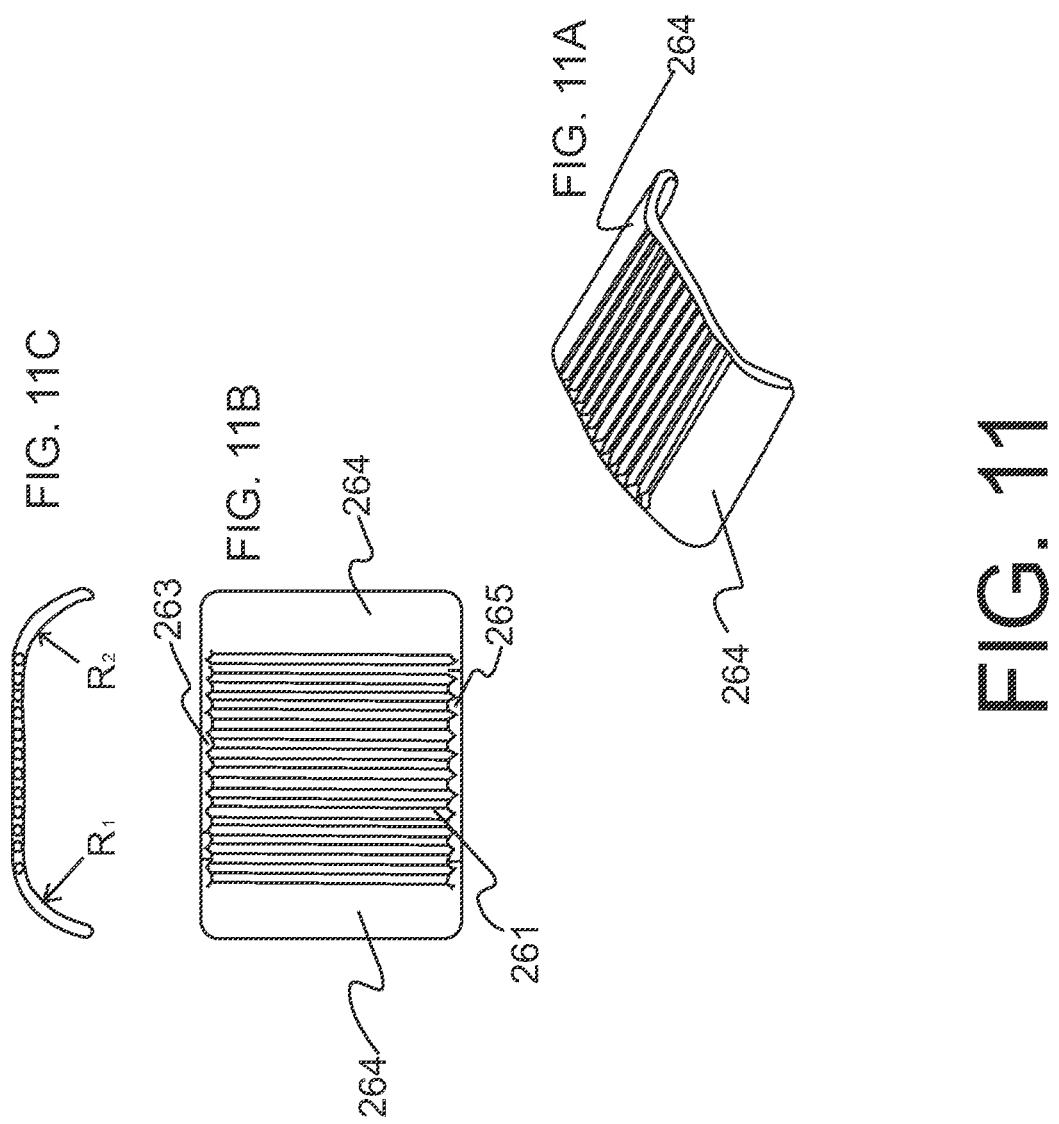

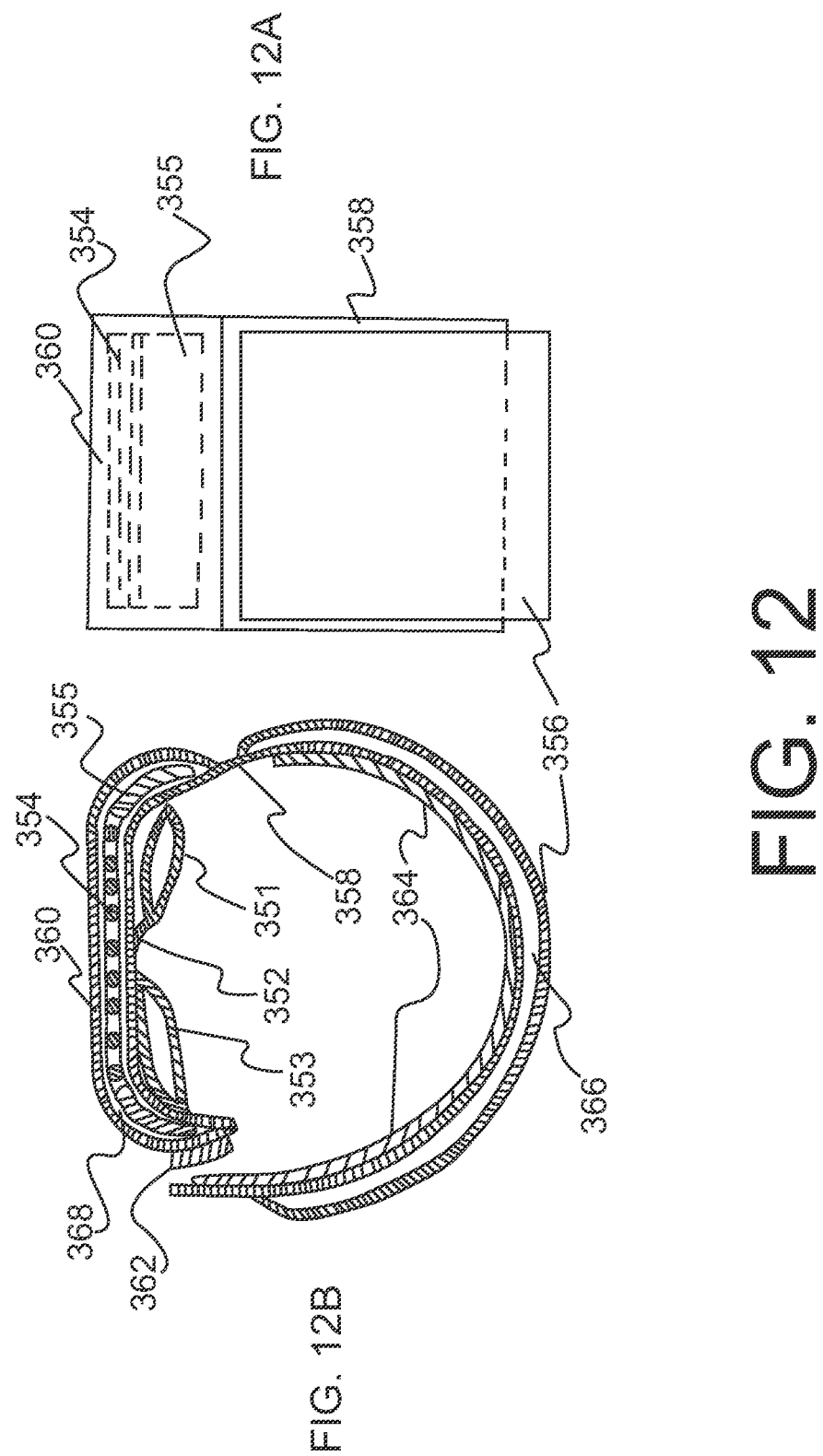

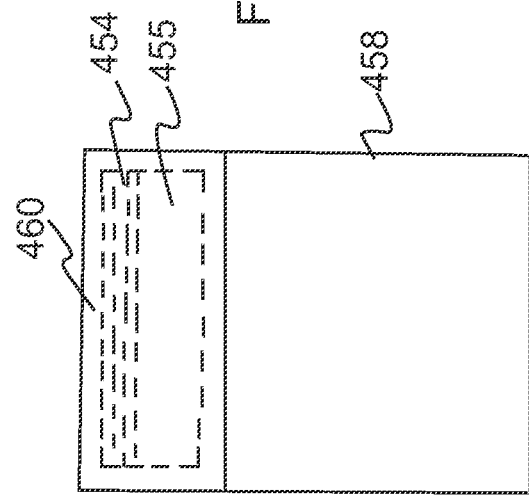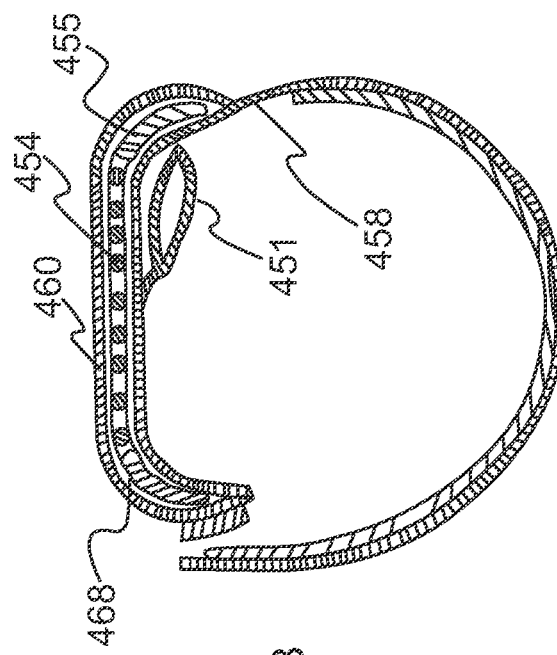

APPARATUS AND METHOD TO STOP BLEEDING

CROSS-REFERENCE TO RELATED APPLICATIONS

This application is a continuation of application
U.S. patent application Ser. No. 16/130,201 filed Sep. 13, 2018, which is a continuation of
U.S. patent application Ser. No. 15/588,586 filed May 5, 2017, now U.S. patent Ser. No. 10/335,161, issued Jul. 2, 2019, which is a continuation of
U.S. patent application Ser. No. 15/150,394 filed May 9, 2016, now U.S. Pat. No. 9,668,744, issued Jun. 6, 2017, which claims priority from and benefit of
Provisional Application No. 62/288,982, filed Jan. 29, 2016, and
which is a continuation-in-part of
U.S. patent application Ser. No. 14/819,383, filed Aug. 5, 2015, now U.S. Pat. No. 9,332,994, issued May 10, 2016, which is a continuation-in-part of
U.S. patent application Ser. No. 13/941,219, filed Jul. 12, 2013, now U.S. Pat. No. 9,308,000, issued Apr. 12, 2016, and which claims priority from and benefit of
U.S. Provisional Patent Application No. 62/089,281, filed Dec. 9, 2014,
U.S. Provisional Patent Application No. 62/096,857, filed Dec. 25, 2014,
U.S. Provisional Patent Application No. 62/103,063, filed Jan. 13, 2015,
U.S. Provisional Patent Application No. 62/142,195, filed Apr. 2, 2015, and
U.S. Provisional Patent Application No. 62/157,419, filed May 5, 2015,
the entire content of all the above listed applications is incorporated herein by reference.

FIELD

Embodiments described herein concern devices and methods for obtaining hemostasis after puncturing a blood pathway, including without limitation puncture of radial or ulnar artery.

BACKGROUND

Blood vessel puncture is commonly needed for performance of endovascular procedures. Smaller caliber arteries, including radial, ulnar and pedal arteries, are easier to manage after the procedure because bleeding can be controlled more easily with external pressure. However, occlusion of these arteries occurs more frequently compared to larger arteries, which frequently results in permanent loss of patency.

Radial artery occlusion refers to the blockage of the radial artery and is a consequence of radial artery cannulation that obliterates the radial artery lumen. Hemostatic devices, which are attached by being wrapped around the portion of an arm where the puncture site (also referred to as the access site) is located and compress the puncture site where bleeding is to be stopped, are already known in the prior art (e.g., U.S. Pat. No. 7,498,477 B2, U.S. Pat. Nos. 8,481,803, 8,481,805, JP 3,031,486 U). In prior-art hemostatic devices, pressure applied to the puncture site may lead to radial artery occlusion making it not available for access in the future.

Radial artery occlusion, after transradial access occurs in 2-10% of patients, and is frequently associated with obliteration of radial artery lumen, making that radial artery not suitable for future access for endovascular procedures, invasive monitoring, or its utility as a bypass conduit. Prevention of radial artery occlusion is of paramount importance to avoid loss of a major source of blood supply, future repeat access and other utilities of radial artery, after transradial access. Maintenance of radial artery flow during hemostatic compression has been shown to lower the risk of radial artery occlusion (PROPHET Trial, Pancholy S et al, Catheterization and Cardiovascular Interventions 2008:72(3); 335-340). A decrease in duration of compression has also been shown to lower the risk of radial artery occlusion (Pancholy S et al, Catheterization and Cardiovascular Interventions 2012:79(1):78-81). Thus maintaining blood flow in the radial artery, while compressing the access site after instrumentation, is known to reduce the risk of post-instrumentation radial artery occlusion. Patent hemostasis is therefore understood to mean achieving the cessation of bleeding at the cannulation wound (access site) of the radial artery, while blood is allowed to flow through that artery.

In an article entitled Efficacy and Safety of Transient Ulnar Artery Compression to Recanalize Acute Radial Artery Occlusion After Transradial Catheterization (Am J Cardiol 2011; 107:1698-1701) Ivo Bernat, MD and others discuss a method directed to open an occluded radial artery after the radial artery becomes occluded. In this study, in patients with radial artery occlusion, 3-4 hours after hemostasis of the radial artery, ulnar artery compression was applied to attempt recanalization of radial artery. Bernat et. al. achieved higher success rates at reopening of the radial artery by administration of heparin and compression of the ipsilateral ulnar artery

SUMMARY

Transradial, as well as transulnar, puncture is increasingly used for obtaining vascular access for endovascular procedures. In one embodiment, a hemostatic device comprises two balloons wherein, after transradial access, the bleeding from the radial artery is stopped by compressing the radial artery at the puncture site using inflation of a first balloon and the radial artery flow is increased by occlusive compression of ipsilateral ulnar artery using inflation of a second balloon. The method maintains blood flow in the radial artery while compressing the access site, after removal of catheter, thereby reducing the risk of post-instrumentation radial artery occlusion. In one embodiment, the first balloon is located over the radial artery to cover a puncture site that is generally about 2 cm. from the base of a palm, and the second balloon is located over the ulnar artery at a position proximate to the base of the palm (Guyon's canal) thereby compressing the ulnar artery at a location where it is most accessible for compression.

In another embodiment, two balloons are part of a band and the band is wrapped around a limb. The center of the first balloon and the center of the second balloon are offset from each other in relation to the central line of axis of the band. In yet another embodiment, the first balloon is larger than the second balloon. In another embodiment, the balloons are rectangular in shape. In one embodiment the first balloon extends the entire width of the band. In one embodiment, the width of the band is greater than 40 mm. In another embodiment, the width of the band is greater than 45 mm. In yet another embodiment, the band has a width of about 55 mm.

In another embodiment, the hemostatic device comprises a flexible band adapted to be wrapped and secured around a hand of a patient at a site on the hand where bleeding is to be stopped, a compression member having an inner peripheral side, which compression member is made of a material more rigid than the band, a first balloon provided on the inner peripheral side at a position deviated to the center portion of the compression member in lengthwise direction of the band, and the first balloon is connected to the band by a connector on a side of the first balloon adjacent the center portion of the compression member, wherein the first balloon inflates when a fluid is introduced therein; and a second balloon provided on the inner peripheral side of the compression member at a position deviated to an edge of the compression member from the center portion of the compression member in widthwise direction of the band, and the second balloon is connected to the band by a connector on a side of the second balloon adjacent to the edge of the compression member, wherein the second balloon inflates when a fluid is introduced therein. In one embodiment, the compression member is a curved frame with rungs. In some embodiments, rungs may be equidistant from each other along the length of the frame. In other embodiments, the rungs may be staggered whereby some rungs are close to each other while the others are spread out. In another embodiment, the frame has rungs in a central portion and curved solid pieces at the proximal and distal end of the frame. In yet another embodiment, the compression member is a curved plate.

In some embodiments, at least a portion of the compression member is curved toward the inner peripheral side at proximal and distal ends of the compression member. In one embodiment, the radius of curvature of the compression member at proximal end is about the same as radius of curvature of the compression member at distal end. In another embodiment, the compression member may have a contoured shape whereby the band presses snugly the wrist and the base of the palm, and the contoured shape facilitates compression of the ulnar artery at the base of the palm.

In one embodiment, the curved compression member possesses a first curved portion in a first half of the compression member located between a center and a first end of the compression member, a second curved portion in a second half of the compression member located between the center and a second end of the curved compression member, and an axis traversing from the first end of the curved compression member, through the center of the compression member, to the second end of the curved compression member. A first balloon is provided on the inner peripheral side in the first half of the curved compression member at a position offset to the center of the curved compression member from the first end of the curved compression member, the first balloon having a plurality of linear sides and is connected to the band by a connector only on a first linear side of the first balloon, said first linear side being adjacent the center of the curved compression member and perpendicular to the axis of the curved compression member. In another embodiment, the first balloon has a first surface and at least a second linear side in contact with the band, wherein the first balloon inflates when a fluid is introduced therein and upon inflation the first surface and at least the second linear side of the first balloon are capable of moving out of contact with the band. In another embodiment, a second balloon is provided on the inner peripheral side in the second half of the curved compression member at a position offset to an edge of the curved compression member from the center of the curved compression member, the second balloon having a plurality of linear sides and is connected to the band by a connector only on a first linear side of the second balloon, said first linear side of the second balloon being adjacent the edge of the curved compression member and parallel to the axis of the curved compression member. In another embodiment, the second balloon has a second surface and at least a second linear side in contact with the band, wherein the second balloon inflates when the fluid is introduced therein and upon inflation the second surface and at least the second linear side of the second balloon are capable of moving out of contact with the band.

In yet another embodiment, the second balloon is provided on the inner peripheral side in the second half of the curved compression member at a position offset to the center of the curved compression member from the second end of the curved compression member, the second balloon having a plurality of linear sides and is connected to the band by a connector only on a first linear side of the second balloon, said first linear side of the second balloon being adjacent the center of the curved compression member and perpendicular to the axis of the curved compression member.

In operation, a method of catheterization of the radial artery comprises inserting a sheath into the radial artery of a patient at an access site. The desired catheterization procedure is then performed using the sheath or catheter to access the radial artery. In one embodiment, once the catheterization procedure is complete, an ulnar pressure is applied to the ipsilateral ulnar artery at an ulnar pressure site while the sheath remains inserted in the radial artery. The sheath is then removed from the radial artery while maintaining the ulnar pressure to the ulnar artery. Once the sheath is removed, and while continuing to apply the ulnar pressure, pressure is applied to the radial artery at the access site to obtain hemostasis at the access site. In another embodiment, once the catheterization procedure is complete, a radial pressure is applied to the radial artery at the access site. An ulnar pressure is then applied to the ulnar artery at the ulnar pressure site while maintaining the pressure on the radial artery. In yet another embodiment, application of pressure to the radial artery at the access site to obtain hemostasis at the access site is accomplished while maintaining the ulnar pressure to the ulnar artery.

In another embodiment, vasodilator medication such as nitroglycerine is disposed on at least a portion of the skin-contacting surface of the balloon pressing on the puncture site to reduce spasm. Spasm may play a role in the process of interruption of the flow, which then leads to thrombosis and resultant lumen obliteration with fibrosis. Prevention and relief of spasm may help lower the probability of occlusion.

In yet another embodiment, a composition is disposed on at least a portion of the skin-contacting region of the balloon. The composition includes at least a hydrocolloid component and an oil component. In one embodiment, a release-coated liner is included on the skin-contacting side of the balloon. The liner is retained in place prior to use and is removed just prior to application to user's skin. The release-coated liner may be any release-coated liner known in the art that is compatible with the composition disposed on the skin-contacting side of the balloon.

BRIEF DESCRIPTION OF DRAWINGS

FIG. 5A is a schematic top view that shows a side of the device that serves as the inside surface when the device is attached to the wrist of a patient. FIG. 5B is a schematic front view of the device.

FIG. 6A shows a schematic sectional front view of an embodiment of the hemostatic device applied on a forearm of a patient. The two balloons 601, 603 are located between the forearm of the patient and the strap 608 that goes around the forearm of the patient. FIG. 6B is a schematic sectional side view of a part of the embodiment of the hemostatic device showing balloon 603 pressing on the ulnar artery 607.

FIG. 8 is a schematic view of an embodiment of the hemostatic device wrapped around the wrist of a patient wherein FIG. 8A is an anterior view and FIG. 8B is a posterior view.

FIG. 11 is a schematic three-dimensional view (FIG. 11A), a schematic top view (FIG. 11B) and a schematic front view (FIG. 11C) of an embodiment of the compression member that is a curved frame with rungs, and comprising rungs 261 located between two curved beams 263 and 265, and curved solid pieces 264 at the proximal and distal end of the frame.

FIG. 12 is a schematic front view (FIG. 12A) and a schematic side view (FIG. 12B) of an embodiment of the hemostatic device comprising at least two balloons 351 and 353, and a compression member that is a curved frame with rungs 354 in a central portion of the frame and curved solid pieces 355 at the proximal and distal end of the frame, the frame being placed in a sleeve 368 formed by a covering 360 attached to a strap 358.

FIG. 13 is a schematic front view (FIG. 13A) and a schematic side view (FIG. 13B) of an embodiment of the hemostatic device comprising at least one balloon 451, and a compression member that is a curved frame with rungs 454 in a central portion of the frame and curved solid pieces 455 at the proximal and distal end of the frame, the frame being placed in a sleeve 468 formed by a covering 460 attached to a strap 458.

DETAILED DESCRIPTION

Figure 1:
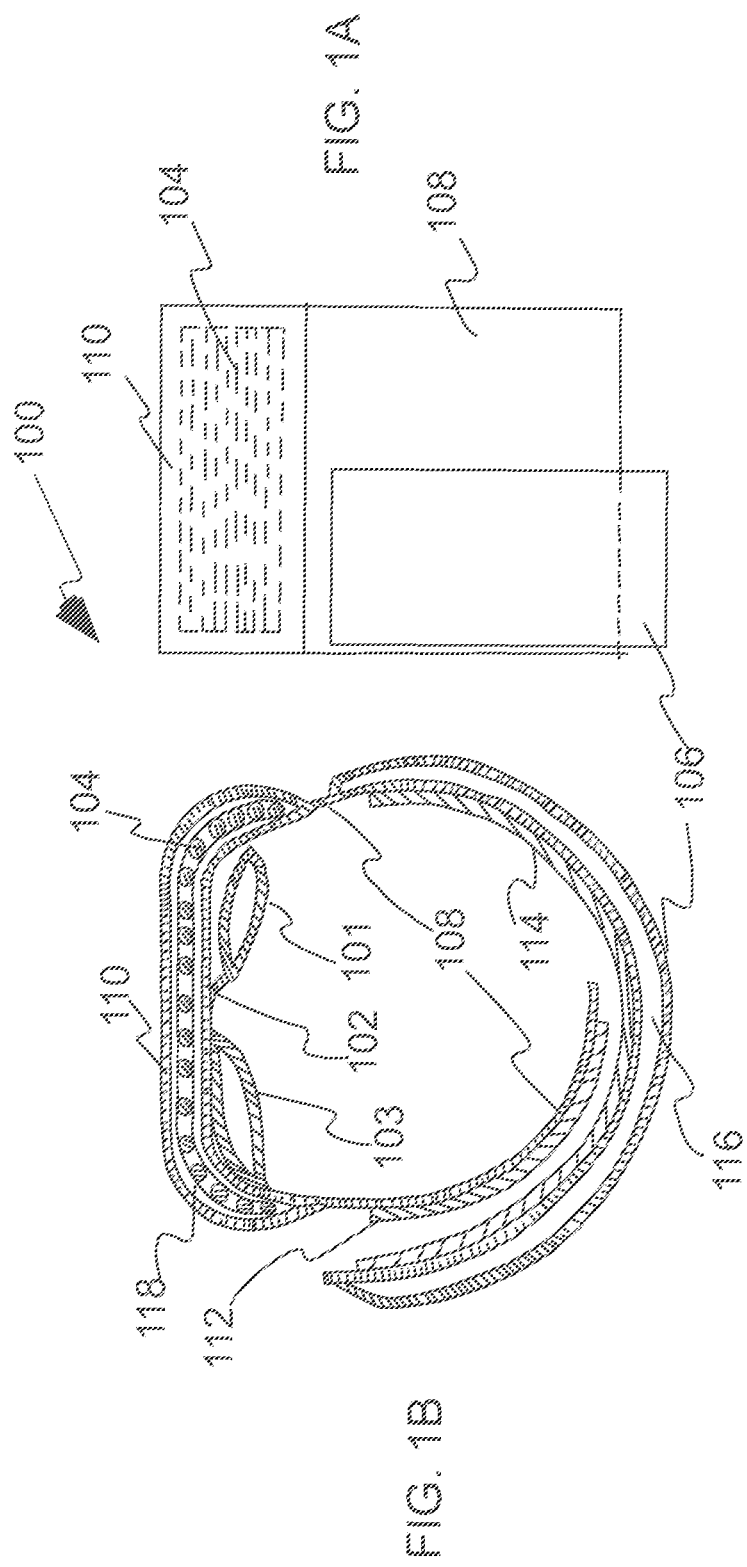
FIG. 1 is a schematic front view (FIG. 1A) and a schematic side view (FIG. 1B) of an embodiment of the hemostatic device 100 comprising at least two balloons 101 and 103, and a compression member that is a curved frame with rungs 104 and that is placed in a sleeve 118 formed by a covering 110 attached to a strap 108.

Embodiments described herein provide the user a safe, simple and reliable device and method to apply pressure at the access site of artery, e.g., radial artery to obtain hemostasis and also to apply pressure to another artery, e.g., ulnar artery using the same device.

In one embodiment of the invention (see FIG. 1), hemostatic device 100 is a flexible band comprising a flexible strap 108 adapted to be wrapped and secured by binders 112 and 114 around the wrist of a patient at a puncture site on the hand where bleeding is to be stopped, a curved frame 104, a first balloon 101, and a second balloon 103. The curved frame 104 has an inner peripheral side and is made of a material such that the frame is more rigid than the flexible strap 108. In one embodiment, the frame is made of hard plastic and substantially fixed in shape. In another embodiment, the frame is made of material (e.g. plastic) that is bendable so that the frame does not maintain a substantially fixed shape and flexes with the balloons as the balloons expand and contract with pressure. In another embodiment, the spacing between the rungs in the frame is increased to make the frame more flexible. In yet another embodiment, the spacing between the rungs in the frame is decreased to make the frame less flexible. At least a portion of the frame is curved toward the inner peripheral side. The first balloon 101 is provided on the inner peripheral side at a position deviated to the center portion of the curved frame from the first end of the curved frame in lengthwise direction of the band, i.e., the first balloon 101 is provided on the inner peripheral side in a first half of the curved frame at a position offset to the center of the curved frame from the first end of the curved frame, and the first balloon is connected to the strap 108 by a connector 102 on a side of the first balloon adjacent the center portion of the curved frame. The first balloon inflates when a fluid is introduced therein. The second balloon 103 is provided on the inner peripheral side of the curved frame at a position deviated to an edge of the curved frame from the center portion of the curved frame in widthwise direction of the band, i.e., the second balloon 103 is provided on the inner peripheral side in a second half of the curved frame at a position offset to an edge of the curved frame from the center of the curved frame, and the second balloon is connected to the strap 108 by a connector (not shown) on a side of the second balloon adjacent the edge of the curved frame. The second balloon 103 inflates when the fluid is introduced therein. In one embodiment, the band 100 is adapted to be wrapped around the wrist with a surface fastener, e.g., Hook and Loop 112 and 114 for securing the band around the wrist. In some embodiments, pledgets (not shown) are provided for patient comfort. In one embodiment, the pledgets are made of foam.

In one embodiment, band may have a first sleeve for holding the frame 104. In the embodiment shown in FIG. 1, the first sleeve is a double layer construction formed by connecting a piece of film 110 to strap 108 of the band at a center portion of the band. The connection may be done by a suitable method such as welding (e.g., heat welding, high-frequency welding, ultrasonic welding) or adhesion/gluing (such as with an adhesive or solvent) so as to form a double layer construction. The frame 104 is inserted into a gap 118 in the double layer and thereby held. In one embodiment, in addition to the center portion of the band, at least one side end portion of the band has a sleeve. As shown in FIG. 1, band may have a second sleeve 116 at a side end portion of the band. The second sleeve is a double layer construction formed by connecting a piece of film 106 to strap 108 of the band. The connection may be done by a suitable method similar to that used for constructing the first sleeve.

The material of construction of the films or sheets used to fabricate the strap, the balloons and the sleeves of the band 100 is preferably substantially transparent whereby patient's arm can be seen through the band. Examples of the material of construction include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicones, polyurethanes various thermoplastic elastomers such as polyamide elastomers, polyurethane elastomers and polyester elastomers, and any combinations of the above in the form of, for example, resin blends, polymer alloys or laminates. The sheet making up the band may be of any suitable thickness. In one embodiment, the thickness of the sheet material is in the range of about 0.1 to about 0.5 mm, and in some embodiments about 0.2 to about 0.3 mm. The band can be secured using hook and loop type fasteners or other suitable fasteners such as buttons, clips and buckles.

The frame 200 (see FIG. 2) is curved at both proximal and distal ends, the curvature being toward an inner peripheral side. In one embodiment, the radius of curvature $R_1$ at the proximal end is substantially the same as the radius of curvature $R_2$ at the distal end. In another embodiment $R_1=R_2$. In another embodiment, the frame is symmetrical about its center. In one embodiment, the frame is constructed of a material more rigid than the band, but maintains some flexibility whereby the frame conforms to the contour of the wrist and flexes with the expansion and contraction of balloons. In another embodiment, the frame maintains a substantially fixed shape.

Figure 2:
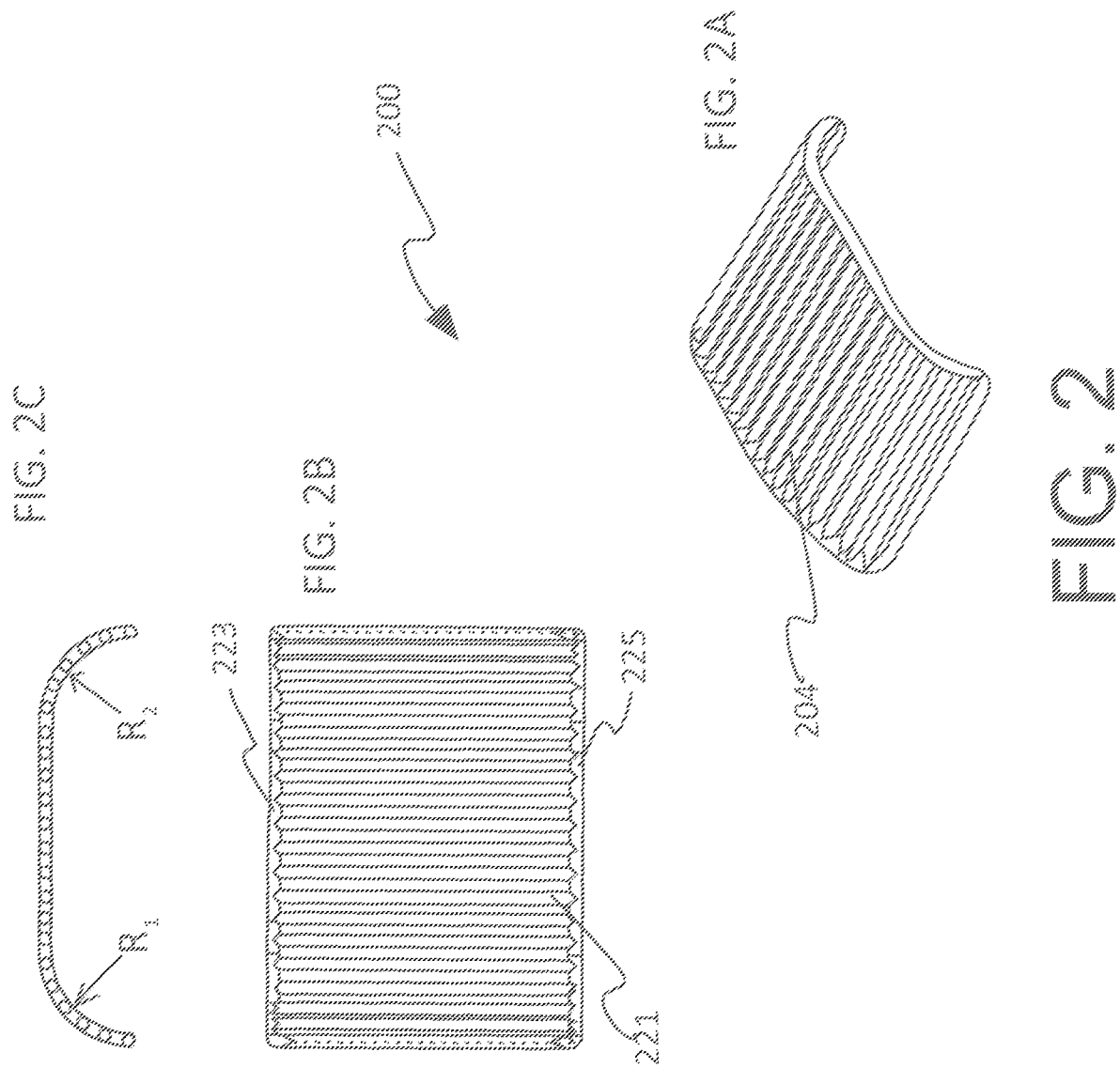
FIG. 2 is a schematic three-dimensional view (FIG. 2A), a schematic top view (FIG. 2B) and a schematic front view (FIG. 2C) of an embodiment of the compression member 200 that is a curved frame with rungs, and comprising rungs 221 located between two curved beams 223 and 225.

In one embodiment, the frame 200 in FIG. 2 may be constructed out of material that is substantially transparent. In another embodiment, the material of construction of the frame may not be transparent. Examples of materials of construction of the frame include acrylic resins, polyvinyl chloride (rigid polyvinyl chloride and flexible polyvinyl chloride), polyolefins such as polyethylene, polypropylene and polybutadiene, polystyrene, poly(4-methyl-1-pentene), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic and aliphatic polyamides, and fluorocarbon resins such as polytetrafluoroethylene. The frame may also be made of a metal or metal alloy.

The curved frame compression member 200 has gaps between the rungs 221 that provide visibility of the puncture site. The rungs are held between two beams 223 and 225. The rungs and beams can have various shapes, e.g., circular, square, rectangular and elliptical. In one embodiment, the frame is entirely curved. In another embodiment, the frame is straight in the center and curved at its ends. In one embodiment, rungs 221 are circular and each rung has a diameter of about 2 mm. In another embodiment, beams 223, 225 are also circular with diameter of about 3 mm. In yet another embodiment, the gap 204 between the rungs is about 2 mm. In one embodiment, the width of the frame is about 4 mm less than the width of the strap 108 of the band 100 in FIG. 1. In yet another embodiment, the gap 204 between the rungs in the center portion of the frame is greater than the gap 204 between the rungs near the proximal and distal ends of the frame. In another embodiment, the curved frame compression member has rungs in the center portion of the frame and solid curved pieces at the proximal and distal ends of the compression member. In one embodiment, the thickness of solid piece is about 2 mm. The width of the solid pieces may be about 4 mm less than the width of the strap of the band, thereby keeping on either side of the curved frame a gap of about 2 mm between the edge of the curved frame and the edge of the strap of the band.

Figure 3:
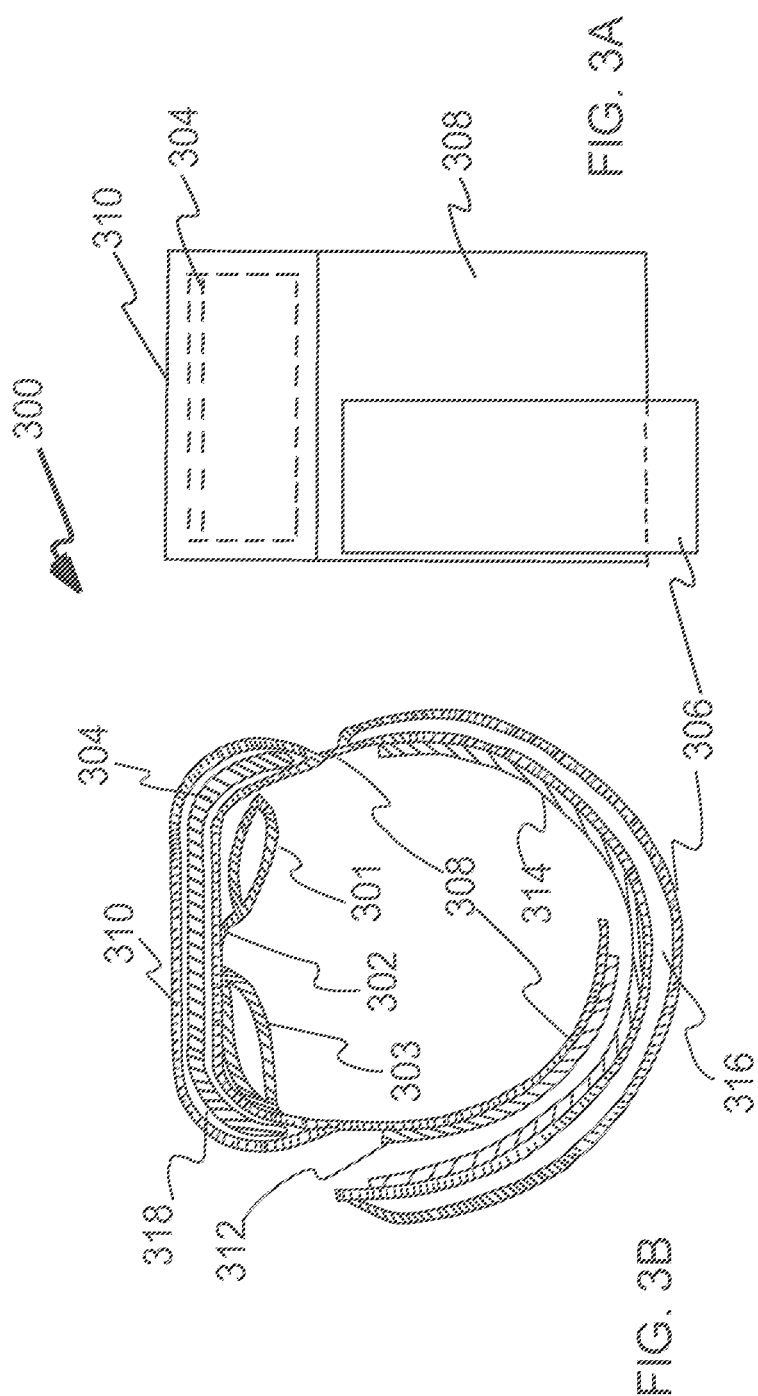
FIG. 3 is a schematic front view (FIG. 3A) and a schematic side view (FIG. 3B) of an embodiment of the hemostatic device 300 comprising at least two balloons 301 and 303, and a compression member that is a curved plate 304 and that is placed in a sleeve 318 formed by a covering 310 attached to a strap 308.

In another embodiment of the invention (See FIG. 3), hemostatic device comprises a flexible band 300. The band has a flexible strap 308 having an inner peripheral side and adapted to be wrapped and secured using binders 312 and 314 around a limb of a patient at a site on the limb where bleeding is to be stopped, a plate 304 made of a material more rigid than the band and at least a portion of the plate is curved toward its inner peripheral side at proximal and distal ends of the plate. In one embodiment, the plate 304 is of substantially fixed shape. In another embodiment, the plate 304 is flexible and does not maintain a substantially fixed shape. The material of construction of plate 304 is same as material of construction of frame 200 discussed before. In one embodiment, the plate 304 is placed in a sleeve 318 formed by a covering 310 attached to the strap 308 on the outer peripheral side of the strap at a center portion of the band. In another embodiment, both the covering 310 and the strap 308 are made of flexible plastic and are transparent. The covering 310 can be attached to strap 308 using known techniques, for example ultrasonic welding. In one embodiment, in addition to the center portion of the band, at least one side end portion of the band has a sleeve 316. The sleeve at a side end portion of the band may also be a double layer construction formed by connecting a piece of film 306 to strap 308 on the outer peripheral side of the strap 308. The connection may be done by a suitable method similar to that used for constructing the sleeve at center portion of the band. The plastic sheet material used to make the strap of the band could also be used to make the sleeves.

The first balloon 301 is provided on the inner peripheral side at a position deviated to the center portion of the curved plate from the first end of the curved plate in lengthwise direction of the band, and the first balloon is connected to the strap 308 by a connector 302 on a side of the first balloon adjacent the center portion of the curved plate. The first balloon inflates when a fluid is introduced therein. The second balloon 303 is provided on the inner peripheral side of the curved plate at a position deviated to an edge of the curved plate from the center portion of the curved plate in widthwise direction of the band, and the second balloon is connected to the strap 308 by a connector (not shown) on a side of the second balloon adjacent the edge of the curved plate. The second balloon 303 inflates when the fluid is introduced therein. In one embodiment, the band 300 is adapted to be wrapped around the wrist with a surface fastener, e.g., Hook and Loop 312 and 314 for securing the band around the wrist.

Figure 4:
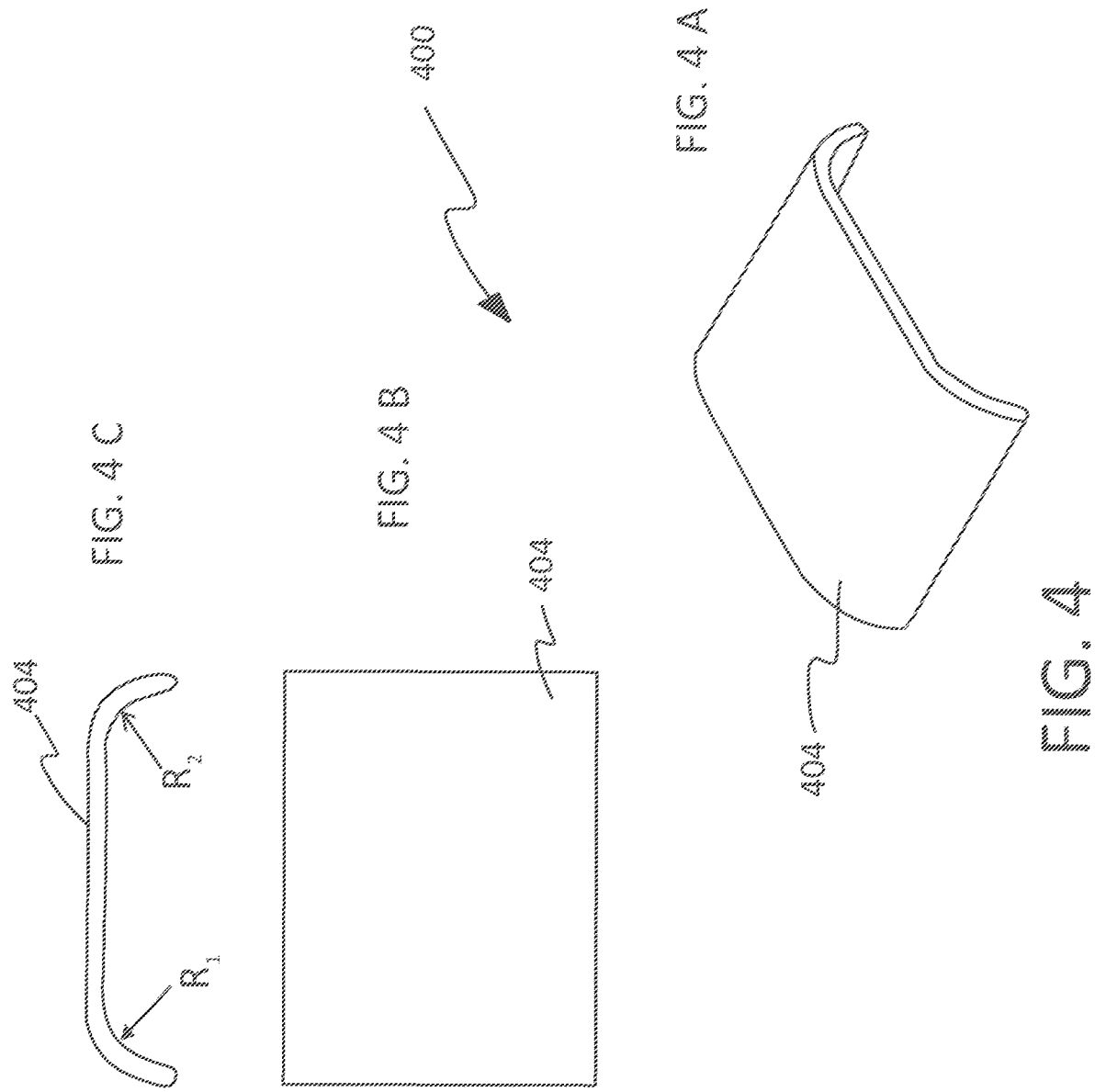
FIG. 4 is a schematic three-dimensional view (FIG. 4A), a schematic top view (FIG. 4B) and a schematic front view (FIG. 4C) of an embodiment of the compression member 400 that is a curved plate.

The plate 400 (see FIG. 4) is curved at both proximal and distal ends, the curvature being toward an inner peripheral side. In one embodiment, the radius of curvature $R_1$ at the proximal end is about the same as the radius of curvature $R_2$ at the distal end. In another embodiment, the plate 404 is symmetrical about its center. In one embodiment, the plate is constructed of a material more rigid than the band, but maintains some flexibility whereby the plate conforms to the contour of the wrist and flexes with the expansion and contraction of balloons. In another embodiment, the plate maintains a substantially fixed shape. The plate 400 may be constructed using same materials as used to construct frame 200 in FIG. 2. In one embodiment, the thickness of plate is about 2 mm. The width of the plate may be about 4 mm less than the width of the strap of the band, thereby keeping on either side of the plate a gap of about 2 mm between the edge of the plate and the edge of the strap of the band.

In another embodiment of the invention (See FIG. 5), hemostatic device 500 comprises a flexible band. The band has a flexible strap 508 having an inner peripheral side and adapted to be wrapped and secured using binders 512 and 514 around a limb of a patient at a site on the limb where bleeding is to be stopped. The band has a center portion and two side portions on either side of the center portion. In one embodiment, the center portion has a first sleeve 518 formed by a covering 510 attached to strap 508. A compression member (not shown) is placed in the first sleeve 518. In one embodiment, the compression member is a curved frame (see FIG. 2). In another embodiment, the compression member is a curved plate (see FIG. 4). In one embodiment, both the covering 510 and the strap 508 are made of flexible plastic and are transparent. The covering 510 can be attached to strap 508 using known techniques, for example ultrasonic welding. A first balloon 501 is provided on the inner peripheral side at a position deviated to the center portion of the first sleeve 518 from the proximal end of the first sleeve in lengthwise direction of the band, and the first balloon is connected to the strap 508 of the band by a connector 502 on a side of the first balloon adjacent the center portion of the first sleeve 518. In one embodiment, the width of the first balloon is about the same as the width of the strap 508 of the band, and the length of the first balloon is about half the length of the first sleeve 518. The first balloon 501 inflates when a fluid is introduced therein. The second balloon 503 is provided on the inner peripheral side of the first sleeve 518 at a position deviated to an edge of the first sleeve from the center portion of the first sleeve in widthwise direction of the band, and the second balloon is connected to the strap 508 of the band by a connector 504 on a side of the second balloon adjacent an edge of the first sleeve 518. The width of the second balloon 503 is about half the width of the strap 508 of the band and the length of the second balloon is about half the length of the first sleeve 518. In another embodiment, the width of the second balloon is about 70% of the width of the band. In yet another embodiment, the width of the second balloon is about 60% of the width of the band. In a further embodiment, the width of the second balloon is about 50% of the width of the band. In another embodiment, the width of the second balloon is about the same as the width of the strap 508 of the band. The second balloon 503 inflates when the fluid is introduced therein.

The compression member possesses a first curved portion in a first half of the compression member located between a center and a first end of the compression member, a second curved portion in a second half of the compression member located between the center and a second end of the compression member, and an axis traversing from the first end of the compression member, through the center of the compression member, to the second end of the compression member. A first balloon 501 is provided on the inner peripheral side in the first half of the compression member at a position offset to the center of the compression member from the first end of the compression member, the first balloon having a plurality of linear sides and is connected to the band by a connector 502 only on a first linear side of the first balloon, said first linear side being adjacent the center of the compression member and perpendicular to the axis of the compression member. In one embodiment, the first balloon has a first surface and at least a second linear side in contact with the band, wherein the first balloon inflates when a fluid is introduced therein and upon inflation the first surface and at least the second linear side of the first balloon are capable of moving out of contact with the band. A second balloon 503 is provided on the inner peripheral side in the second half of the compression member at a position offset to an edge of the compression member from the center of the compression member, the second balloon having a plurality of linear sides and is connected to the band by a connector 504 only on a first linear side of the second balloon, said first linear side of the second balloon being adjacent the edge of the compression member and parallel to the axis of the compression member. In another embodiment, the second balloon has a second surface and at least a second linear side in contact with the band, wherein the second balloon inflates when the fluid is introduced therein and upon inflation the second surface and at least the second linear side of the second balloon are capable of moving out of contact with the band.

In yet another embodiment, the second balloon is provided on the inner peripheral side in the second half of the curved compression member at a position offset to the center of the curved compression member from the second end of the curved compression member, the second balloon having a plurality of linear sides and is connected to the band by a connector only on a first linear side of the second balloon, said first linear side of the second balloon being adjacent the center of the curved compression member and perpendicular to the axis of the curved compression member.

The material of construction of the balloons is preferably transparent and may be the same as used to make the band. In one embodiment, the material of construction of the balloon could be sheets of thickness similar to that used to make the strap of the band. In another embodiment, the sheets used to make balloons could be thinner than the sheets used to make the strap of the band. In one embodiment, the strap is made of polyvinyl chloride film of thickness 20 mils (0.508 mm) and a balloon is made of polyvinyl chloride film of thickness 10 mils (0.254 mm). The balloons could have any shape such as square, rectangular, circular and elliptical. The balloons can be made by sealing sheet cut to appropriate shape and sealed at the edge using sealing technique such as adhesion or welding. The balloons are connected to the band by flexible connectors 502 and 504 that could be made of same material as the balloon and the band. In one embodiment, the band and the compression member are substantially transparent. In another embodiment, the balloon 503 is made of translucent or opaque material and the balloon 501 is made of substantially transparent material.

Figure 5:
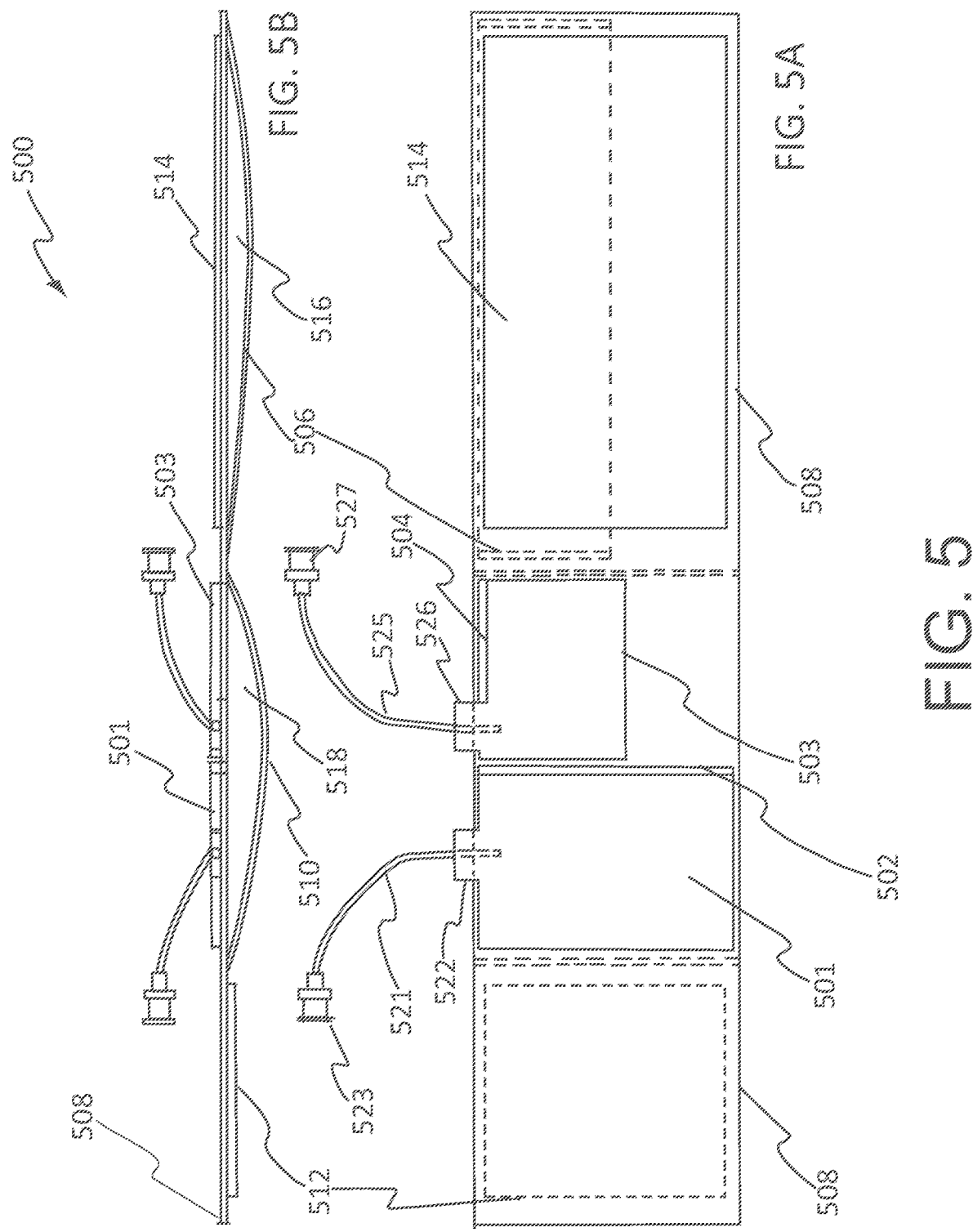
FIG. 5 is a schematic view of hemostatic device 500 with two balloons 501 and 503.

As shown in FIG. 5, the first balloon 501 has connected thereto a tube 521 for introducing a fluid into the first balloon, and the second balloon 503 has connected thereto a tube 525 for introducing a fluid into the second balloon. In one embodiment, the tubes are transparent and flexible. Tube 521 is connected at a proximal end thereof to the first balloon 501 at 522. Tube 525 is connected at a proximal end thereof to the second balloon 503 at 526. Tube 521 may include an adapter 523 that is connected to the distal side of the tube, and tube 525 may include an adapter 527 that is connected to the distal side of the tube. In one embodiment, adapter 523 is identifiably different from adapter 527 so that a user knows to select the appropriate adapter that connects to the balloon user wants to inflate. The identifiable differentiation of the adapters may be through visual distinction comprising color, shape, texture or combination thereof. Inflation of the balloon is carried out by inserting the protruding tip of a syringe (not shown) into the adapter and pushing a plunger on the syringe so as to introduce fluid within the syringe through the inflator into the balloon. Once fluid has been injected into the balloon and the protruding tip of the syringe is withdrawn from the adapter, a check valve within the adapter closes, preventing the fluid from leaking out and thus maintaining the balloon in an inflated state. In another embodiment, a two-way or three-way valve is used to direct the flow of fluid into and out of the balloon, and to prevent the fluid from leaking out and thus maintaining the balloon in an inflated state.

In one embodiment, in addition to the center portion of the band, at least one side end portion of the band has a sleeve. As shown in FIG. 5, the band may have a second sleeve 516 at one side end portion of the band. The second sleeve is a double layer construction formed by connecting a piece of film 506 to strap 508 of the band. The connection may be done by a suitable method similar to that used for constructing the first sleeve. The second sleeve 516 may be used to hold tubes 521, 525 and adapters 523, 527 when the band is wrapped around the wrist of a patient (See FIG. 8). In one embodiment, the width of the second sleeve 516 is less than the width of the band. In another embodiment, the width of the second sleeve 516 is about the same as the width of the band.

The technique of providing a compression member on the band is not limited to the illustrated arrangement, and may involve joining the compression member(s) to the inside surface or outside surface of the band by a suitable method such as welding or adhesion. It is not necessary that the band encircle the limb, e.g., wrist completely. For example, another arrangement may be the band is held in place by tie down that holds the band firmly on the wrist. In another embodiment, the band does not have any compression member to enhance rigidity.

Figure 6:
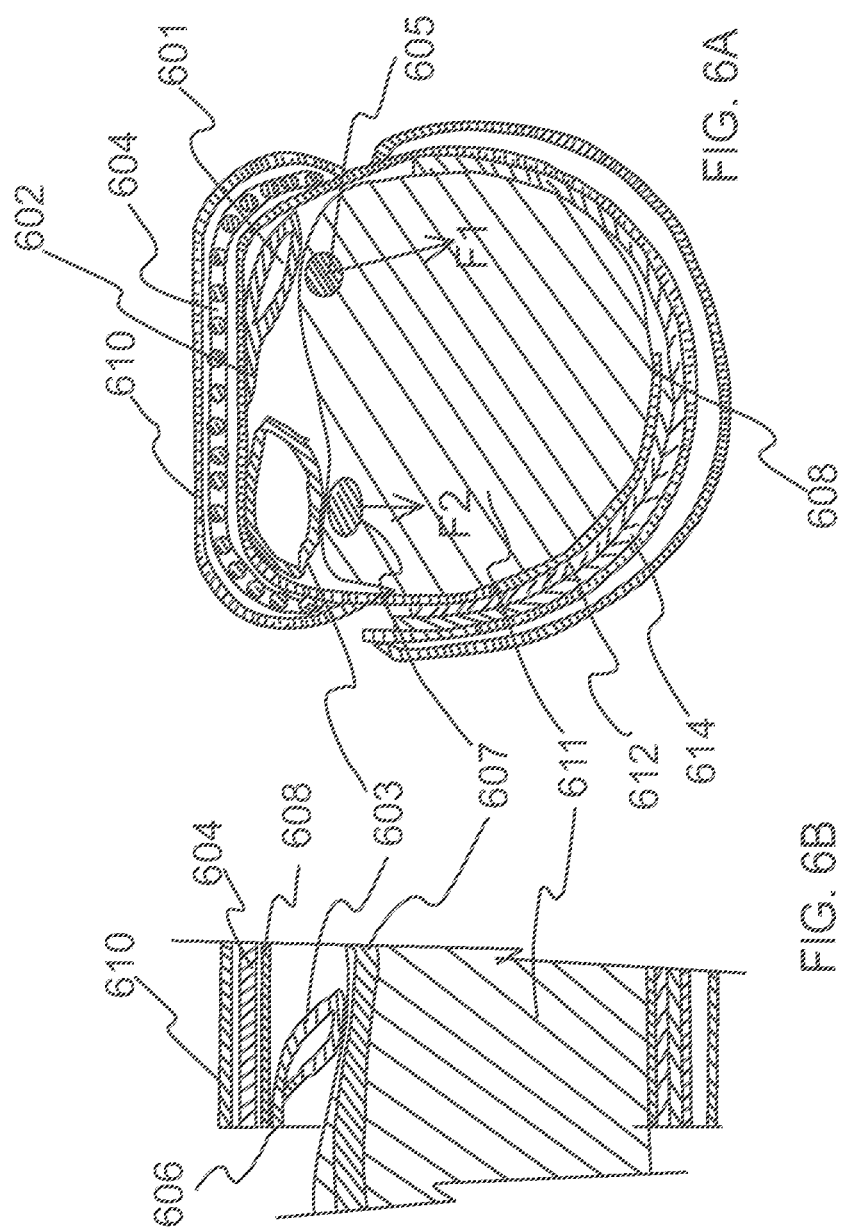
FIG. 6 is schematic sectional view showing hemostatic device of FIG. 1 in use.

FIG. 6 is a sectional view showing a band in a wrapped state to the wrist 611. The band is attached to the wrist by connecting together surface fasteners (e.g. hook and loop fasteners) 612 and 614. Other means for securing the band in a wrapped state around the wrist include buttons, clips, snaps, zippers, and buckles through which the ends of the band pass. A frame 604 is placed in a sleeve formed by a covering 610 attached to the strap 608 on the outer peripheral side of the strap at a center portion of the band. One side of balloon 601 is connected to the strap 608 of the band by connector 602 at a position deviated to the center portion of the curved frame 604 from the end of the curved frame in lengthwise direction of the band. As a result, the balloon assumes an orientation whereby the pressing force F1 applied to the puncture site on the radial artery 605 acts generally in an outward direction away from the center portion of the wrist (See FIG. 6A). Consequently, force F1 does not have an impact at the location of the ulnar artery 607. On the other hand, if the balloon 601 was connected to the band at a position deviated to the end of the curved frame, the balloon would assume an orientation whereby the pressing force would be in an oblique direction towards the center portion of the wrist whereby a component of the force F1 would affect the ulnar artery 607.

The ulnar artery 607 is compressed by balloon 603, which is provided on the inner peripheral side of the curved frame 604 at a position deviated to an edge of the curved frame from the center portion of the curved frame in widthwise direction of the band, and balloon 603 is connected to the band by a connector 606 on a side of balloon 603 adjacent to an edge of the curved frame 604 (see FIG. 6B). In the present embodiment where one side of balloon 603 is connected by a connector at an edge of the band and the width of the balloon 603 is shorter than the width of the strap 608, balloon 603 assumes an orientation whereby component of the force F2 in the cross-sectional plane of the wrist is generally vertical (see FIG. 6A). The force F2 may have a component in a direction towards the elbow, but a negligible component in a direction towards the radial artery. Therefore, operation of balloon 603 to pressurize or depressurize the ulnar artery will not generally affect operation of balloon 601 to pressurize or depressurize the radial artery, and vice versa.

Figure 7:
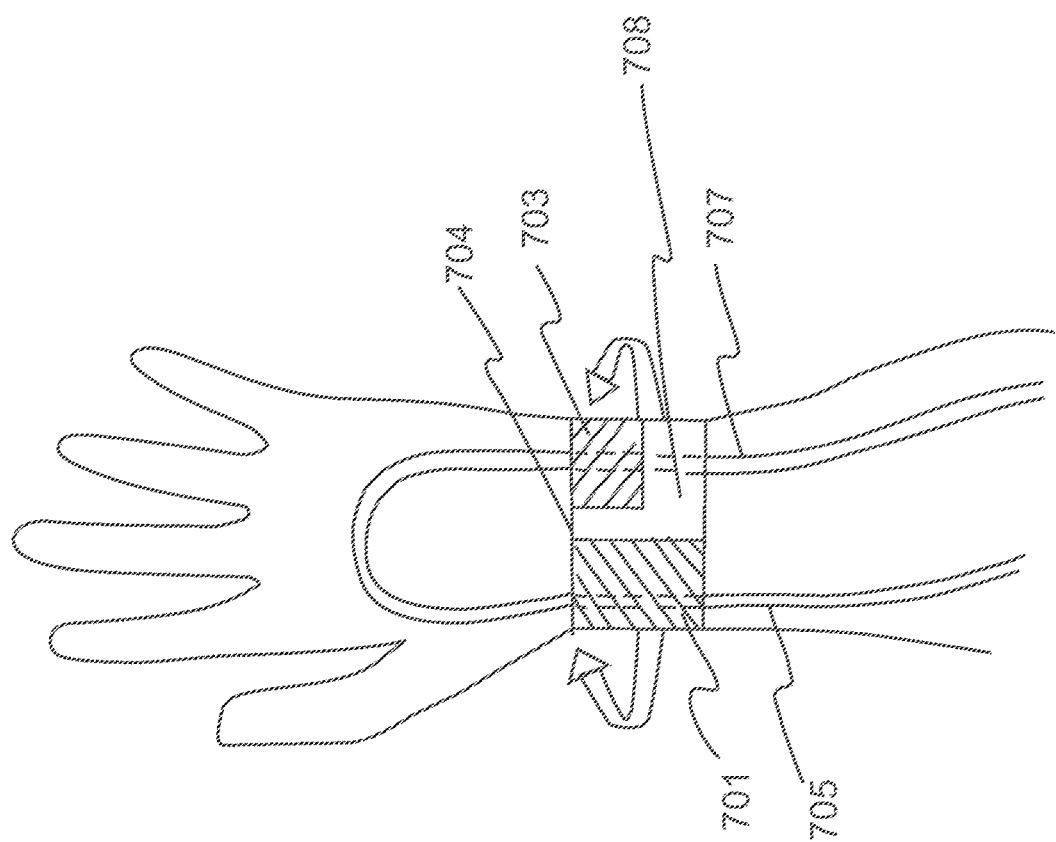
FIG. 7 is a schematic view of an embodiment of the hemostatic device showing placement of balloon 701 over radial artery 705 and balloon 703 over ulnar artery 707.

FIG. 7 is a schematic of a band 708 wrapped around a wrist whereby balloon 701 compresses the radial artery 705 and balloon 703 compresses the ulnar artery 707. In the embodiment in FIG. 7, the balloon 703 is located at or near the base of the palm (Guyon's canal) 704 thereby compressing the ulnar artery 707 at a location where it is most accessible for compression and the balloon 701 is located over the puncture site, which is generally about 2 cm. from the base of a palm. The pressure applied to the radial artery and the ulnar artery could be simultaneously and independently manipulated to optimize the pressure at which the bleeding from the radial artery stops while at the same time a high enough pressure is applied to the ulnar artery to prevent or minimize occlusion of the radial artery. In one embodiment, mark or marks (not shown) may be placed on the radial balloon 701 to help a user visually place a central portion of the radial balloon 701 on the radial artery 705 at or near the puncture site of the artery. Mark or marks may also be placed on the compression member and the sleeve holding the compression member to help a user in the placement of the radial balloon 701 on the puncture site. Mark may be a dot, a line, a square, a triangle or any other shape that helps in the placement.

Figure 8:
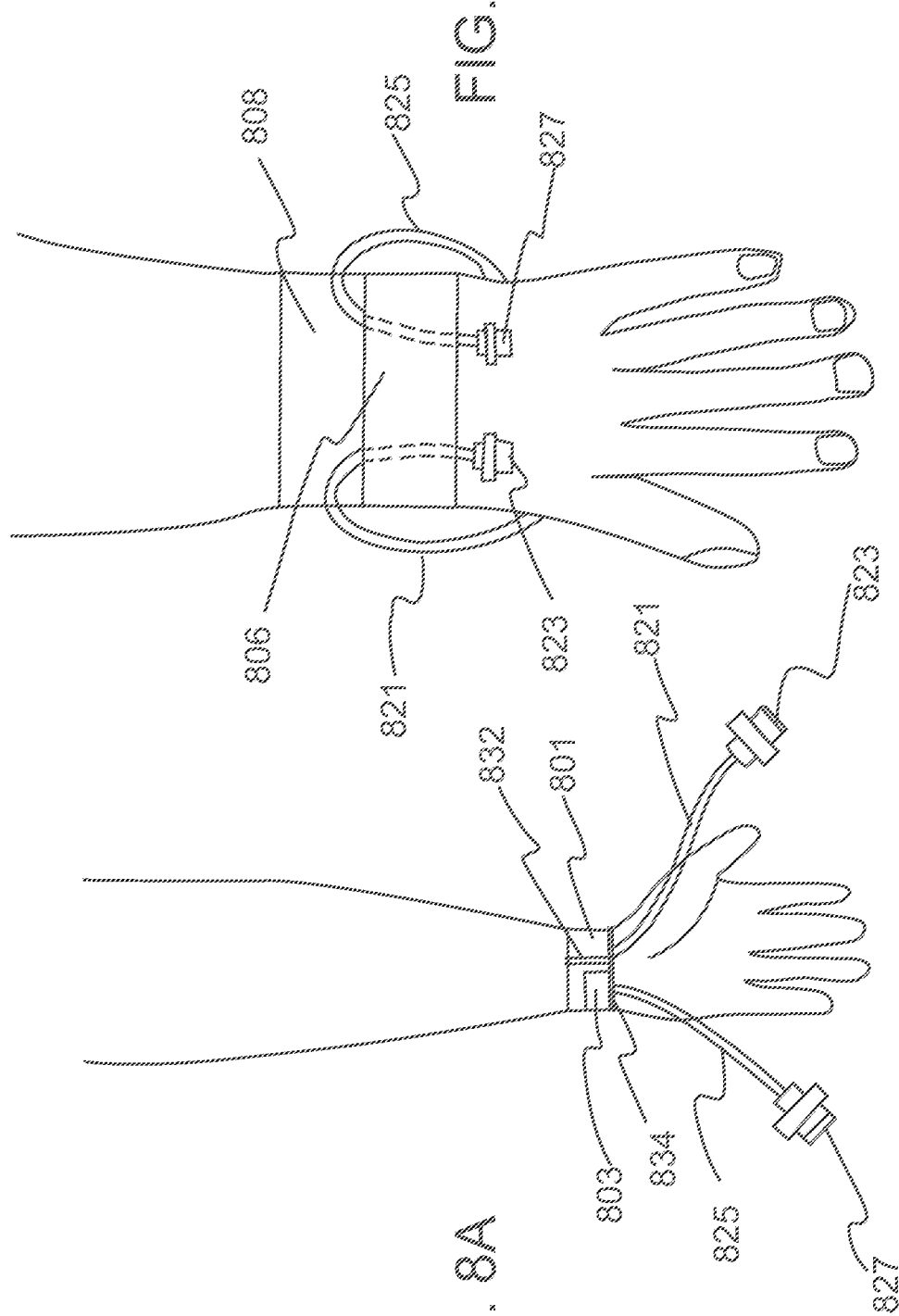

FIG. 8 is a schematic illustration showing an anterior view (FIG. 8A) and a posterior view (FIG. 8B) of an embodiment of a band 808 wrapped around the wrist of a patient. One side of radial balloon 801 is connected to the band by connector 832 such that the connector 832 is positioned towards the center portion of the wrist. The radial balloon 801 is inflated or deflated by passing fluid (a gas such as air or a liquid such as saline) through tube 821 using a syringe (not shown) that is connected to adapter 823. The ulnar balloon 803 is inflated or deflated by passing fluid (a gas such as air or a liquid such as saline) through tube 825 using a syringe (not shown) that is connected to adapter 827. A balloon will inflate when a fluid is introduced therein, thereby applying pressure to the skin of the patient where the balloon is located. In one embodiment, the fluid is introduced using a syringe. The syringe may have markers to determine the amount of fluid that will be inserted into a balloon. The syringe may also have an outlet that can be connected to a pressure measuring device such as a manometer. In another embodiment, the balloons may have an outlet that can be connected to a pressure measuring device. The pressure measurement helps the user to inflate the balloon to a pressure that is not significantly higher than the systolic pressure of the patient, thereby allowing robust hemostasis but preventing grossly excessive compression by inordinate pressure, thereby lowering the probability of lumen compression to the point of occlusion, and flow cessation.

The edge of the band is positioned close to the base of the palm 834. The band 808 may have a sleeve 806 at a side end portion of the band. The sleeve is a double layer construction and tubes 821, 825 and adapters 823 and 827 may be inserted in the sleeve 806 so that the tubes do not dangle when a patient moves his/her hand.

Figure 9:
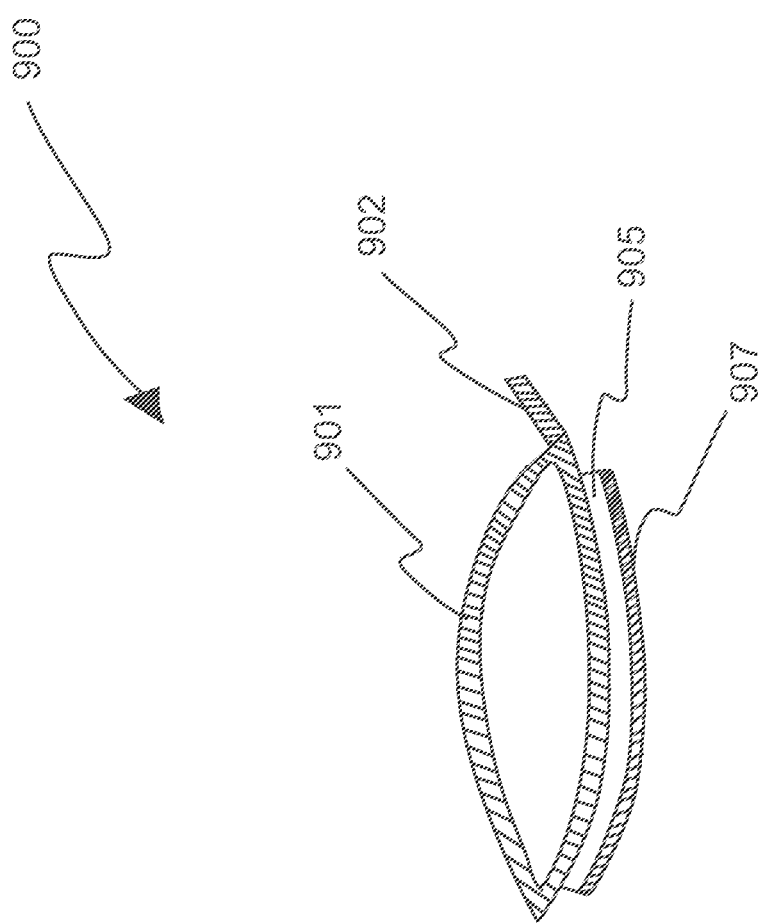
FIG. 9 is a schematic view of a balloon 900 wherein a surface of the balloon to be in contact with skin is disposed with a composition 905 and a liner 907.

FIG. 9 shows an embodiment of balloon 900 where the surface of the balloon 901 in contact with skin is coated with a composition 905. In one embodiment, composition 905 may comprise a hydrocolloid adhesive or zinc oxide-based adhesive that can be advantageously used upon the surface of the balloon when pressing the balloon on the skin of the patient. The hydrocolloid or zinc oxide-based adhesive can be used either alone or in combination with another medical grade adhesive. Hydrocolloid and zinc oxide-based adhesives have less of a tendency to excoriate the skin of a patient when removed. This can be particularly important for patients whose skin is more sensitive or fragile. In one embodiment, the coated composition 905 has a peel-off laminate (liner) 907 that is removed before placing the balloon on the puncture site. In another embodiment, the composition also contains antimicrobials. In one embodiment, the composition contains oil. Such compositions are known in the art and commercially available. See, e.g., compositions and laminates sold by Vancive Medical Technologies, Avery Dennison business. In some embodiments, connector 902 may be provided to connect the balloon to the band. In another embodiment, vasodilator medication is present on the surface of a balloon pressing on the puncture site to reduce spasm. Spasm is thought to play a role in the process of interruption of the flow that then leads to thrombosis and resultant lumen obliteration with fibrosis. Prevention and relief of spasm may help lower the probability of occlusion. An example of such vasodilator medication is nitroglycerine. In one embodiment, the surface of balloon in contact with the puncture site is disposed with nitroglycerine.

Figure 10:
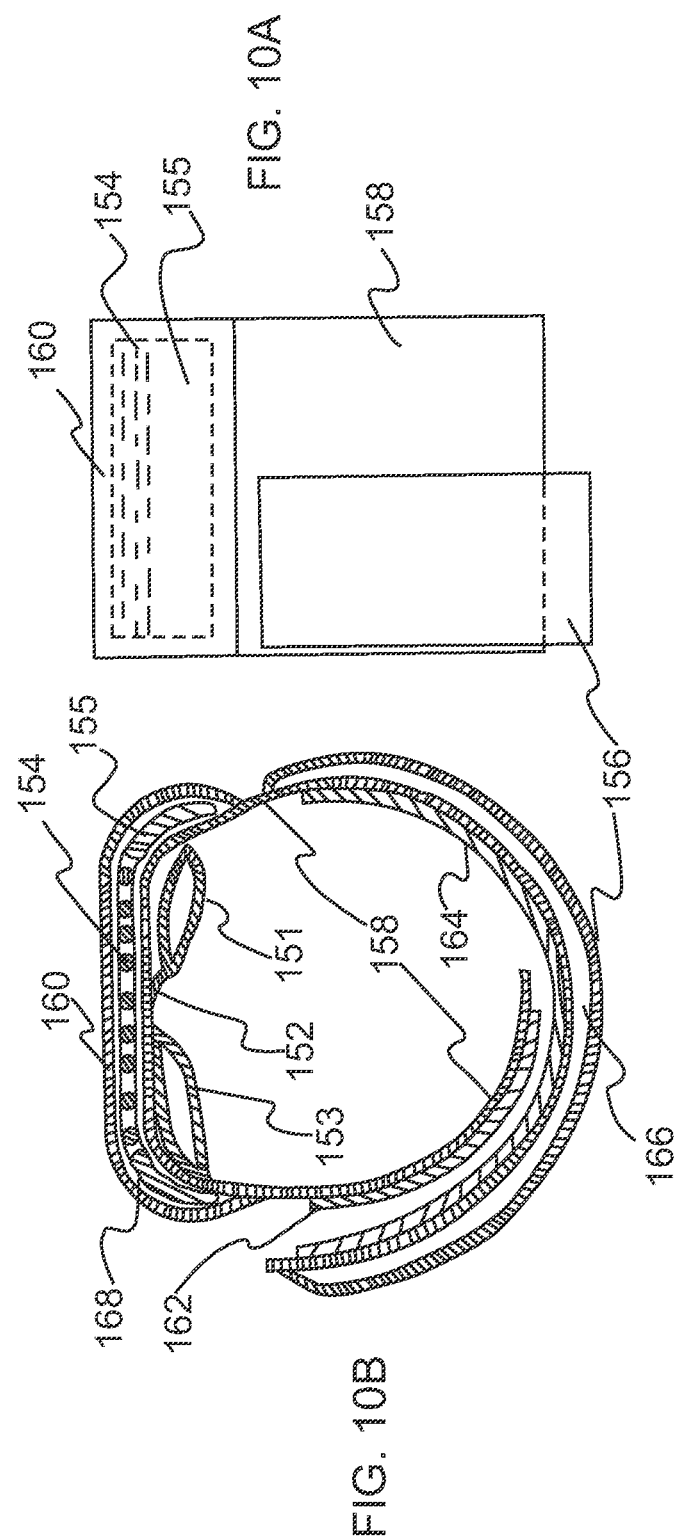
FIG. 10 is a schematic front view (FIG. 10A) and a schematic side view (FIG. 10B) of an embodiment of the hemostatic device comprising at least two balloons 151 and 153, and a compression member that is a curved frame with rungs 154 in a central portion of the frame and curved solid pieces 155 at the proximal and distal end of the frame, the frame being placed in a sleeve 168 formed by a covering 160 attached to a strap 158.

An embodiment of the hemostatic device depicted in FIG. 10 is similar to that depicted in FIG. 1, except that the hemostatic device in FIG. 10 uses an embodiment of the frame depicted in FIG. 11. The embodiment of frame depicted in FIG. 11 comprises a plurality of rungs 261 in the center portion of the frame and curved solid pieces 264 at the proximal and distal ends of the frame. The balloon 151 is connected to the strap 158 by a connector 152 on a side of the balloon 151 adjacent the center portion of the curved frame. As shown in FIG. 10, in one embodiment, the band may have a second sleeve 166 at a side end portion of the band. The second sleeve is a double layer construction formed by connecting a piece of film 156 to strap 158 of the band. In another embodiment, the band may not have a second sleeve. Two fasteners 162 and 164 holds the band around a wrist of a patient.

In another embodiment of the hemostatic device (see FIG. 12), a fastener 362 is located on the covering 360 attached to a strap 358. The covering 360 forms a sleeve 368 to hold the frame. A fastener 364 is located on the strap 358 and connecting the two fasteners 362 and 364 holds the band around a wrist of a patient. In yet another embodiment, the covering 360 may be a continuous portion of the strap 358 turned to loop around the frame, thereby forming a sleeve to hold the frame. The balloon 351 is connected to the strap 358 by a connector 352 on a side of the balloon 351 adjacent the center portion of the curved frame. As shown in FIG. 12, in one embodiment, the band may have a second sleeve 366 at a side end portion of the band. The second sleeve is a double layer construction formed by connecting a piece of film 356 to strap 358 of the band. In another embodiment, the band may not have a second sleeve. An embodiment of the hemostatic device depicted in FIG. 13 is similar to that depicted in FIG. 12, except that the embodiment in FIG. 13 has a single balloon 451 to press on the radial artery.

An embodiment of the band of the present invention is used in a method directed at minimizing occurrences of radial artery occlusion during the catheterization procedure of the radial artery. In one embodiment, once the catheterization procedure is complete, an ulnar pressure is applied to the ipsilateral ulnar artery at an ulnar pressure site while a sheath, e.g., a catheter, remains inserted in the radial artery. The sheath is then removed from the radial artery while maintaining the pressure to the ulnar artery. Once the sheath is removed, and while continuing to apply the ulnar pressure, pressure is applied to the radial artery at the access site to obtain hemostasis at the access site. In another embodiment, once the catheterization procedure is complete, a radial pressure is applied to the radial artery at the access site. The radial pressure may be applied while a sheath, e.g., a catheter, remains inserted in the radial artery or after the sheath is removed from the radial artery. An ulnar pressure is then applied to the ipsilateral ulnar artery at an ulnar pressure site. In one embodiment, the ulnar pressure is continuously and simultaneously applied with the radial pressure to obtain hemostasis of the radial artery. In another embodiment, ulnar pressure is gradually reduced to zero before obtaining hemostasis. In yet another embodiment, the pressures applied to the radial artery and the ulnar artery are simultaneously and independently manipulated to optimize the pressure at which the bleeding from the radial artery stops while at the same time a high enough pressure is applied to the ulnar artery to prevent or minimize occlusion of the radial artery.

The radial pressure is applied by inflating a radial balloon, e.g., balloon 601 in FIG. 6. The radial balloon is positioned over the access site of the radial artery 605. Upon inflation of the radial balloon, the radial balloon assumes an orientation whereby the pressing force applied to the puncture site on the radial artery 605 acts generally in an outward direction away from the center portion of the wrist. The pressing force applied to the puncture site on the radial artery 605 is directionally away from the ulnar artery. Upon inflation of the ulnar balloon, the pressing force on the ulnar artery may have a component in a direction towards the elbow, but a negligible component in a direction towards the radial artery. The pressing force applied on the ulnar artery is directionally away from the radial artery. Therefore, operation of the ulnar balloon 603 to pressurize or depressurize the ulnar artery 607 will not generally affect operation of balloon 601 to pressurize or depressurize the radial artery 605, and vice versa.

The radial artery and the ulnar artery are the two conduits for the flow of oxygenated blood to the hand. The arteries are interconnected and therefore form an interdependent flow network. When flow is reduced in one of the arteries, by compression for example, flow increases in the other artery. When the ulnar artery is compressed, flow in the ulnar artery is reduced, which causes an increase in pressure and flow in the radial artery.

In an embodiment, a further step includes confirming that the application of ulnar pressure has reduced blood flow through the ulnar artery. This is done by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in one embodiment.

In another embodiment, the method further includes confirming patency of the radial artery during the step of applying a pressure to the radial artery. Confirmation of patency is accomplished by sensing skin blood flow and/or pulsation at a fingertip or other location downstream of the access site. Other sensing locations both upstream and downstream may be used to confirm patency of the radial artery. In one embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Metric is understood to mean a sensible, quantifiable value or reading, relating to the characteristic sensed. Digital plethysmography may be employed to obtain the metrics. Other sensing modes may be employed, so long as the selected mode is capable of confirming patency in one form or another.

Example 1

A band was fabricated from a substantially transparent polyvinyl chloride sheet material having a thickness of 0.5 mm. The band had a length of 240 mm and a width of 55 mm. A radial artery balloon and an ulnar artery balloon were each fabricated from a substantially transparent polyvinyl chloride sheet material having a thickness of 0.25 mm. The radial artery balloon had the dimension of 38 mm×55 mm and the ulnar artery balloon had the dimension of 38 mm×38 mm. The radial artery balloon, ulnar artery balloon and band were welded together at the necessary places to form a hemostatic device having the construction according to FIG. 5. Two adapters with check valves were connected to the two balloons via ducts as shown in FIG. 5. A curved frame was made of 2 mm diameter rungs, with spacing between the rungs of 2 mm (center to center distance between the rungs was 4 mm). The rungs were held between two parallel beams of diameter 3 mm. The frame was curved at both ends, and had identical radius of curvature at both ends. The radius of curvature at each end was 20 mm. The frame had a center portion that was straight and had a length of 28 mm. The width of the frame was 52 mm. The frame was constructed according to FIG. 2. Hook and loop (Velcro) fasteners were used to fasten. This hemostatic device was wrapped around the wrist of normal volunteers and the two balloons were inflated by injecting air into the balloons using a 20 mL syringe with a luer lock. It was observed that inflation of the radial balloon did not influence perfusion of the fingers via the ulnar artery. A 20 mL inflation of the radial artery balloon lead to complete obliteration of antegrade radial flow, although there was no influence on perfusion through the ulnar artery. On the ulnar side, with a shorter width (38 mm) balloon, full 15 mL inflation of ulnar balloon did not influence the status of flow in the radial artery.

Any constricting girdle-like device would be expected, even at a lower pressure to first constrict the veins and cause venous congestion in the fingers. It was surprising to observe a complete lack of venous congestion, and no symptoms of venous congestion were reported by any of the volunteers. On several occasions, 2 hour application of the band was performed as would be performed clinically for hemostasis. Venous congestion did not occur. Symptoms related to pressure at the ulnar tuberosity were also not reported by the volunteers. This is likely because of (i) focal pressure application by the orientation of the balloons, leaving probably enough soft tissue space (in the central compartment of the forearm where most large veins are located) for the venous return to occur, and (ii) a decrease in magnitude of required pressure because of the design features such as orientation and sizes of the two balloons, their location in the band, and the shape and structure of the frame.

Comparative Example 2

A band similar to that used in EXAMPLE 1 was fabricated, the only difference being, in COMPARATIVE EXAMPLE 2, the width of the ulnar balloon was nearly the same as the width of the band. In EXAMPLE 1, the ulnar balloon had a width of 38 mm, which is about 70% of the width of the band. With the larger ulnar balloon of COMPARATIVE EXAMPLE 2, inflation of the ulnar balloon was noted to influence the perfusion of radial artery. This was particularly pronounced in small forearms where the larger ulnar balloon may assume an orientation such that the force applied to the wrist when the ulnar balloon is inflated impacts the radial artery.

Tests have shown that the location of the ulnar balloon on the forearm aspect of the band increased the efficacy of the balloon to compress and occlude ulnar artery. Moving the balloon towards the hand and especially gluing it to the palmar aspect of the band increased the efficacy of the ulnar balloon to focally compress and occlude ulnar artery without any other effects or symptoms.

An embodiment of the band of the present invention may also be used in a method directed at minimizing occurrences of ulnar artery occlusion during the catheterization procedure of the ulnar artery. In one embodiment, once the catheterization procedure is complete, a radial pressure is applied to the radial artery at a radial pressure site while a sheath, e.g., a catheter, remains inserted in the ulnar artery. The sheath is then removed from the ulnar artery while maintaining the pressure to the radial artery. Once the sheath is removed, and while continuing to apply the radial pressure, pressure is applied to the ulnar artery at the access site to obtain hemostasis at the access site. In another embodiment, once the catheterization procedure is complete, an ulnar pressure is applied to the ulnar artery at the access site. The ulnar pressure may be applied while a sheath, e.g., a catheter, remains inserted in the ulnar artery or after the sheath is removed from the ulnar artery. A radial pressure is then applied to the radial at a radial pressure site. In one embodiment, the radial pressure is continuously and simultaneously applied with the ulnar pressure to obtain hemostasis of the ulnar artery. In another embodiment, radial pressure is gradually reduced to zero before obtaining hemostasis of the ulnar artery. In yet another embodiment, the pressures applied to the radial artery and the ulnar artery are simultaneously and independently manipulated to optimize the pressure at which the bleeding from the ulnar artery stops while at the same time a high enough pressure is applied to the radial artery to prevent or minimize occlusion of the ulnar artery.

An embodiment of the band of the present invention may also be used in a method directed to obtaining hemostasis of both radial and ulnar artery when catheterization procedures are simultaneously performed on both radial and ulnar arteries.

It will be appreciated that several of the above-disclosed and other features and functions, or alternatives or varieties thereof, may be desirably combined into many other different systems or applications. Also that various alternatives, modifications, variations or improvements therein may be subsequently made by those skilled in the art which are also intended to be encompassed by the following claims.

In the description above, for the purposes of explanation, numerous specific requirements and several specific details have been set forth in order to provide a thorough understanding of the embodiments. It will be apparent however, to one skilled in the art, that one or more other embodiments may be practiced without some of these specific details. The particular embodiments described are not provided to limit the invention, but to illustrate it. The scope of the invention is not to be determined by the specific examples provided above. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. In another situation, an inventive aspect may include a combination of embodiments described herein or in a combination of less than all aspects described in a combination of embodiments.

The invention claimed is:

1. A hemostatic device configured to be applied to a limb of a patient, the hemostatic device comprising:
a flexible band to be applied to the limb of the patient in a wrapped state in which the flexible band is wrapped around at least a portion of the limb of the patient to apply the hemostatic device to the limb of the patient at a site where bleeding is to be stopped;
means for securing the band in the wrapped state to the patient's limb;
a member more rigid than the flexible band, the member and the flexible band being connected to each other so that when the flexible band is in the wrapped state the member is positioned on the limb of the patient at the site on the limb where bleeding is to be stopped, the member possessing an inner peripheral side which faces toward a surface of the limb of the patient when the flexible band is in the wrapped state, the member also possessing an outer peripheral side opposite the inner peripheral side;
at least one portion of the inner peripheral side of the member being a curved portion that is curved toward the inner peripheral side, and other portion of the inner peripheral side of the member being a flat portion, the member possessing a lengthwise extent and including opposite ends that are spaced apart along the lengthwise extent of the member to define first and second ends of the member, the member also possessing a center with respect to the lengthwise extent of the member, the curved portion of the inner peripheral side of the member being located between the first end of the member and the center of the member with respect to the lengthwise extent of the member;
an inflatable balloon that is inflatable upon introducing fluid into the balloon, the inflatable balloon being on the inner peripheral side of the member;
the inflatable balloon being connected to the flexible band at a position adjacent the center of the member so that when the flexible band is in the wrapped state and the balloon is inflated the balloon orients towards the first end of the member, and at least a first portion of the inflatable balloon being positioned at the curved portion of the inner peripheral side of the member such that the curved portion and the first portion of the inflatable balloon overlie one another, at least a part of the flat portion of the member and at least a second portion of the balloon overlying one another when the flexible band is in the wrapped state and the balloon is inflated so that the balloon applies a compressive force to the site in an oblique direction with respect to the surface of the limb, the compressive force pointing outwards away from the center of the limb, the part of the flat portion being a flat section having spaced apart ends; the inner peripheral side of the flat section of the flat portion of the member lying in a plane, the balloon being positioned on one side of the plane and the outer peripheral side of the flat portion of the member being positioned on an opposite side of the plane; and the first end of the member and at least a part of the curved portion of the inner peripheral side of the member being positioned on the one side of the plane.

2. The hemostatic device according to claim 1, wherein the member is a frame.

3. The hemostatic device according to claim 1, wherein the member is a substantially transparent frame.

4. The hemostatic device according to claim 1, wherein the member possesses a longitudinal extent, the flexible band overlapping at least a part of the longitudinal extent of the member.

5. The hemostatic device according to claim 1, wherein the flexible band includes a first part that extends beyond the first end of the member and a second part that extends beyond the second end of the member.

6. The hemostatic device according to claim 1, wherein the member and the flexible band are connected to one another by virtue of a gap formed between two layers of the flexible band, and the member being positioned in the gap.

7. The hemostatic device according to claim 1, wherein the flexible band is transparent to allow the site where bleeding is to be stopped to be viewed through the transparent flexible band, the transparent flexible band including a holder defined by a gap located between first and second spaced apart portions of the transparent flexible band, the member more rigid than the flexible band being positioned in the gap so that the inner peripheral side of the member faces the first portion of the transparent flexible band while an outer peripheral side of the member faces the second portion of the transparent flexible band.

8. The hemostasis device according to claim 1, wherein the hemostasis device comprises medication to apply to the puncture site.

9. The hemostasis device according to claim 8, wherein the medication is selected from a group including antimicrobials, vasodilators, and combinations thereof.

10. A hemostatic device configured to be applied to a limb of a patient, the hemostatic device comprising:
   a flexible band to be applied to the limb of the patient in a wrapped state in which the flexible band is wrapped around at least a portion of the limb of the patient to apply the hemostatic device to the limb of the patient at a site where bleeding is to be stopped;
   means for securing the band in the wrapped state to the patient's limb;
   a member more rigid than the flexible band, the member and the flexible band being connected to each other so that when the flexible band is in the wrapped state the member is positioned on the limb of the patient at the site on the limb where bleeding is to be stopped, the member possessing an inner peripheral side which faces toward a surface of the limb of the patient when the flexible band is in the wrapped state;
   at least one portion of the inner peripheral side of the member being a curved portion that is curved toward the inner peripheral side, and other portion of the inner peripheral side of the member being a flat portion, the member possessing a lengthwise extent and including opposite ends that are spaced apart along the lengthwise extent of the member to define first and second ends of the member, the member also possessing a center with respect to the lengthwise extent of the member, the curved portion of the inner peripheral side of the member being located between the first end of the member and the center of the member with respect to the lengthwise extent of the member;
   an inflatable balloon that is inflatable upon introducing fluid into the balloon, the inflatable balloon being connected to the flexible band, the balloon being on the inner peripheral side of the member, the inflatable balloon being connected to the flexible band at a position adjacent the center of the member so that when the flexible band is in the wrapped state and the balloon is inflated the balloon orients towards the first end of the member; and
   a first portion of the inflatable balloon being positioned at a center portion of the inner peripheral side of the member such that the center portion and the first portion of the inflatable balloon overlie one another, the first portion of the inflatable balloon being a substantial portion of the inflatable balloon so that the balloon applies a compressive force to the site in an oblique direction with respect to the surface of the limb, the compressive force pointing outwards away from the center of the limb.

11. The hemostatic device according to claim 10, wherein the member is a frame.

12. The hemostatic device according to claim 10, wherein the member is a substantially transparent frame.

13. The hemostatic device according to claim 10, wherein the flexible band includes a first part that extends beyond the first end of the member and a second part that extends beyond the second end of the member.

14. The hemostatic device according to claim 10, wherein the member and the flexible band are connected to one another by virtue of a gap formed between two layers of the flexible band, and the member being positioned in the gap.

15. The hemostatic device according to claim 10, wherein the flexible band is transparent to allow the site where bleeding is to be stopped to be viewed through the transparent flexible band, the transparent flexible band including first and second spaced apart portions between which is positioned the member that is more rigid than the flexible band, the first portion of the transparent flexible band possessing an outer surface facing the member that is more rigid than the flexible band and an opposite inner surface facing the surface of the limb when the flexible band is in the wrapped state, the second portion of the transparent flexible band possessing an inner surface contacting the member that is more rigid than the flexible band and an opposite outer surface, one part of the first portion of the transparent flexible band being positioned between the member that is more rigid than the flexible band and the balloon when the flexible band is in the wrapped state and the balloon is inflated, the outer surface of the one part of the first portion of the transparent flexible band contacting both the inner peripheral side of a part of the curved portion of the member and the inner peripheral side of a part of the flat portion of the member when the flexible band is in the wrapped state and the balloon is inflated.

16. The hemostatic device according to claim 10, wherein at least a part of the curved portion of the member that is more rigid than the flexible band and at least a second portion of the balloon overlie one another when the flexible band is in the wrapped state and the balloon is inflated.

* * * * *